(12) United States Patent
Nakao et al.

(10) Patent No.: US 12,422,747 B2
(45) Date of Patent: *Sep. 23, 2025

(54) NEGATIVE PHOTOSENSITIVE RESIN COMPOSITION, PATTERN FORMATION METHOD, AND LAMINATED FILM

(71) Applicants: SAN-APRO LTD., Kyoto (JP); TOKYO OHKA KOGYO CO., LTD., Kawasaki (JP)

(72) Inventors: Takuto Nakao, Kyoto (JP); Tomoyuki Shibagaki, Kyoto (JP); Yuji Nakamura, Kyoto (JP); Kenichi Yamagata, Kawasaki (JP); Takahiro Kondo, Kawasaki (JP); Masahiro Masujima, Kawasaki (JP); Hirofumi Imai, Kawasaki (JP)

(73) Assignees: SAN-APRO LTD., Kyoto (JP); TOKYO OHKA KOGYO CO., LTD., Kawasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/003,623

(22) PCT Filed: Jun. 2, 2021

(86) PCT No.: PCT/JP2021/021027
§ 371 (c)(1),
(2) Date: Dec. 28, 2022

(87) PCT Pub. No.: WO2022/009569
PCT Pub. Date: Jan. 13, 2022

(65) Prior Publication Data
US 2023/0236505 A1 Jul. 27, 2023

(30) Foreign Application Priority Data
Jul. 8, 2020 (JP) .................. 2020-117686

(51) Int. Cl.
*G03F 7/004* (2006.01)
*C07C 303/32* (2006.01)
*C07C 381/12* (2006.01)
*C07D 335/16* (2006.01)
*G03F 7/021* (2006.01)
*G03F 7/038* (2006.01)
*G03F 7/30* (2006.01)
(Continued)

(52) U.S. Cl.
CPC .......... *G03F 7/0045* (2013.01); *C07C 303/32* (2013.01); *C07C 381/12* (2013.01); *C07D 335/16* (2013.01); *G03F 7/0217* (2013.01); *G03F 7/0382* (2013.01); *G03F 7/0385* (2013.01); *G03F 7/32* (2013.01); *G03F 7/425* (2013.01); *G03F 7/426* (2013.01)

(58) Field of Classification Search
CPC .... G03F 7/0382; G03F 7/0217; G03F 7/0045; G03F 7/0385; G03F 7/038; G03F 7/004; G03F 7/40; G03F 7/32; G03F 7/325; G03F 7/425; G03F 7/426; G03F 7/20; C07D 333/78; C07D 335/16; C07C 381/12
USPC ....................................... 430/270.1
See application file for complete search history.

(56) References Cited

U.S. PATENT DOCUMENTS 3,981,897 A 9/1976 Crivello
4,058,400 A 11/1977 Crivello
(Continued)

FOREIGN PATENT DOCUMENTS

CN 101952269 1/2011
CN 104081279 A 10/2014
(Continued)

OTHER PUBLICATIONS

International Search Report issued in International Application No. PCT/JP2021/021027, mailed Aug. 3, 2021.
(Continued)

*Primary Examiner* — John S. Chu
(74) *Attorney, Agent, or Firm* — KNOBBE, MARTENS, OLSON & BEAR, LLP

(57) ABSTRACT

A negative photosensitive resin composition containing an epoxy group-containing resin and a cationic polymerization initiator which includes a sulfonium salt represented by General Formula (I0). In Formula (I0), R1 and R2 represent an aryl group, a heterocyclic hydrocarbon group, or an alkyl group. R3 to R5 are an alkyl group, a hydroxy group, an alkoxy group, an alkylcarbonyl group, an arylcarbonyl group, an acyloxy group, an arylthio group, an alkylthio group, an aryl group, a heterocyclic hydrocarbon group, an aryloxy group, a hydroxy(poly)alkyleneoxy group, or a halogen atom. k is an integer of 0 to 4, m is an integer of 0 to 3, and n is an integer of 1 to 4. A is a group represented by —S—, —O—, —SO—, —SO₂—, or —CO— X⁻ represents a monovalent polyatomic anion.

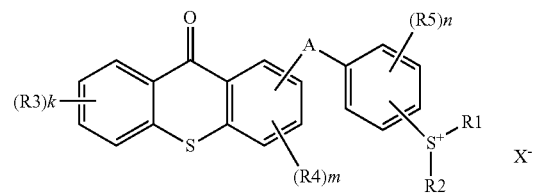

10 Claims, No Drawings

(51) Int. Cl.
  *G03F 7/32* (2006.01)
  *G03F 7/42* (2006.01)

(56) References Cited

U.S. PATENT DOCUMENTS

| | | |
|---|---|---|
| 4,058,401 A | 11/1977 | Crivello |
| 4,069,055 A | 1/1978 | Crivello |
| 4,069,056 A | 1/1978 | Crivello |
| 4,136,102 A | 1/1979 | Crivello |
| 4,150,988 A | 4/1979 | Crivello |
| 4,161,405 A | 7/1979 | Crivello |
| 4,161,478 A | 7/1979 | Crivello |
| 4,173,551 A | 11/1979 | Crivello |
| 4,175,963 A | 11/1979 | Crivello |
| 4,175,972 A | 11/1979 | Crivello |
| 4,175,973 A | 11/1979 | Crivello |
| 4,192,924 A | 3/1980 | Crivello |
| 4,219,654 A | 8/1980 | Crivello |
| 4,234,732 A | 11/1980 | Crivello |
| 4,250,311 A | 2/1981 | Crivello |
| 4,273,668 A | 6/1981 | Crivello |
| 4,283,312 A | 8/1981 | Crivello |
| 4,329,306 A | 5/1982 | Crivello |
| 4,407,759 A | 10/1983 | Crivello |
| 4,417,061 A | 11/1983 | Crivello |
| 6,093,753 A | 7/2000 | Takahashi |
| 6,723,483 B1 | 4/2004 | Oono et al. |
| 9,268,222 B2 | 2/2016 | Takahashi et al. |
| 11,809,078 B2 * | 11/2023 | Imaizumi ............... G03F 7/038 |
| 2003/0207201 A1 | 11/2003 | Hatakeyama et al. |
| 2003/0235779 A1 | 12/2003 | Hatakeyama et al. |
| 2010/0297540 A1 | 11/2010 | Hayoz et al. |
| 2011/0039205 A1 * | 2/2011 | Suzuki ................... G03F 7/004 |
| | | 430/270.1 |
| 2011/0300482 A1 | 12/2011 | Suzuki et al. |
| 2014/0099581 A1 | 4/2014 | Inagaki et al. |
| 2018/0143534 A1 | 5/2018 | Takahashi |
| 2019/0235380 A1 | 8/2019 | Nakamura et al. |
| 2019/0300476 A1 | 10/2019 | Fukunaga et al. |
| 2020/0201181 A1 | 6/2020 | Imai et al. |

FOREIGN PATENT DOCUMENTS

| | | | |
|---|---|---|---|
| CN | 104918914 | | 9/2015 |
| CN | 107229185 | | 10/2017 |
| CN | 111061126 | A | 4/2020 |
| JP | 50-151997 | | 12/1975 |
| JP | 2-178303 | | 7/1990 |
| JP | 8-165290 | | 6/1996 |
| JP | 9-118663 | | 5/1997 |
| JP | 2009-269849 | | 11/2009 |
| JP | 2013-178492 | A | 9/2013 |
| JP | 2018-036533 | A | 3/2018 |
| JP | 2020-101718 | A | 7/2020 |
| TW | 201708947 | | 3/2017 |
| TW | 201917166 | A | 5/2019 |
| WO | WO 2009/136482 | | 11/2009 |
| WO | WO 2010/095385 | | 8/2010 |
| WO | WO 2012/176750 | A1 | 12/2012 |
| WO | WO2017212963 | A1 | 12/2017 |
| WO | WO 2018/003470 | A1 | 1/2018 |
| WO | WO-2019111796 A1 * | | 6/2019 .......... B32B 15/043 |
| WO | WO 2020/145043 | A1 | 7/2020 |

OTHER PUBLICATIONS

Office Action received in Taiwanese Patent Application No. 110120617 mailed Sep. 25, 2024.
International Search Report issued Feb. 18, 2020 in International (PCT) Application No. PCT/JP2019/049093.
Office Action received in U.S. Appl. No. 17/419,504 mailed on Dec. 26, 2023.
Office Action received in U.S. Appl. No. 17/419,504 mailed on May 10, 2024.

* cited by examiner

NEGATIVE PHOTOSENSITIVE RESIN COMPOSITION, PATTERN FORMATION METHOD, AND LAMINATED FILM

CROSS-REFERENCE TO RELATED APPLICATIONS

This application is the U.S. National Phase under 35 U.S.C. § 371 of International Application PCT/JP2021/021027, filed Jun. 2, 2021, designating the U.S., and published in Japanese as WO 2021/131522 on Jul. 1, 2021 which claims priority to Japanese Patent Application No. 2020-117686 filed Jul. 8, 2020, the entire content of which is incorporated herein by reference.

PARTIES TO JOINT RESEARCH AGREEMENT

The present invention was made pursuant to a joint research agreement between Tokyo Ohka Kogyo Co., Ltd. and San-Apro.

TECHNICAL FIELD

The present invention relates to a negative photosensitive resin composition, a pattern formation method, and a laminated film. Priority is claimed on Japanese Patent Application No. 2020-117686, filed on Jul. 8, 2020, the content of which is incorporated herein by reference.

BACKGROUND ART

In recent years, with miniaturization and high density of electronic parts, there is an increasing demand for a photosensitive resin composition used in electronic parts having a hollow sealing structure, such as a surface acoustic wave (SAW) filter. In a formation of the hollow sealing structure of the electronic part, a cured film obtained by curing a photosensitive resin composition needs to be thin and hard.

In addition, the photosensitive resin composition is also used as a spacer (wall material) between a semiconductor wafer and a transparent substrate. For example, a negative photosensitive resin composition is used to form a photosensitive resin film on a surface of a semiconductor wafer or the like, the photosensitive resin film is selectively exposed to radiation such as light and electron beams, and then a pattern is formed by performing a development treatment and pressure-bonded to a transparent substrate (for example, a glass substrate) or the like to form a spacer. In a case where the photosensitive resin film is developed by a photolithography method, it is required that a film having a thickness required for the spacer is formed and it is possible to perform a high-resolution patterning with a favorable shape and no residue.

As a photosensitive material for forming the photosensitive resin film, in the related art, a photosensitive resin composition which contains an epoxy resin having two or more epoxy groups in one molecule, an alkali-soluble resin, and a cationic polymerization initiator is disclosed (see Patent Document 1).

CITATION LIST

Patent Document

[Patent Document 1]
PCT International Publication No. WO2012/176750

SUMMARY OF INVENTION

Technical Problem

As the miniaturization and high density of electronic parts having a hollow sealing structure continue to advance, it is important to form a thick film and a fine-sized pattern in forming the hollow sealing structure.

However, in the photosensitive resin composition in the related art, such as the photosensitive resin composition disclosed in Patent Document 1, in a case where miniaturization of the pattern which is to be a spacer of the hollow sealing structure is attempted, there is a problem in poor resolution.

The present invention has been made in consideration of the above-described problem, and an object of the present invention is to provide a negative photosensitive resin composition having higher resolution, a pattern formation method using the negative photosensitive resin composition, and a laminated film using the negative photosensitive resin composition.

Solution to Problem

In order to solve the above-described problem, the present invention employs the following configurations.

That is, a first aspect of the present invention is a negative photosensitive resin composition containing an epoxy group-containing resin (A) and a cationic polymerization initiator (I), in which the cationic polymerization initiator (I) includes a sulfonium salt (I0) represented by General Formula (I0).

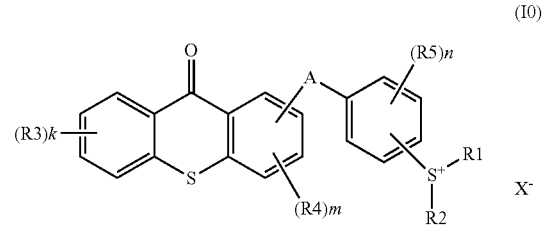

[in Formula (I0), R1 and R2 each represent an aryl group having 6 to 30 carbon atoms, a heterocyclic hydrocarbon group having 4 to 30 carbon atoms, or an alkyl group having 1 to 30 carbon atoms, in which a part of hydrogen atoms in the aryl group, the heterocyclic hydrocarbon group, or the alkyl group may be substituted with a substituent (t), the substituent (t) being at least one selected from the group consisting of an alkyl group having 1 to 18 carbon atoms, a hydroxy group, an alkoxy group having 1 to 18 carbon atoms, an alkylcarbonyl group having 2 to 18 carbon atoms, an arylcarbonyl group having 7 to 11 carbon atoms, an acyloxy group having 2 to 19 carbon atoms, an arylthio group having 6 to 20 carbon atoms, an alkylthio group having 1 to 18 carbon atoms, an aryl group having 6 to 10 carbon atoms, a heterocyclic hydrocarbon group having 4 to 20 carbon atoms, an aryloxy group having 6 to 10 carbon atoms, a hydroxy(poly)alkyleneoxy group represented by HO($-R^A$O)q- {$R^A$ O represents an ethyleneoxy group and/or a propyleneoxy group and q represents an integer of 1 to 5}, and a halogen atom, R3 to R5 are each an alkyl group, a hydroxy group, an alkoxy group, an alkylcarbonyl group, an arylcarbonyl group, an acyloxy group, an arylthio group, an alkylthio group, an aryl group, a heterocyclic hydrocarbon group, an aryloxy group, a hydroxy(poly)alkyleneoxy group, or a halogen atom, k, m, and n represent the numbers of R3, R4, and R5, in which k is an integer of 0 to 4, m is an integer of 0 to 3, and n is an integer of 1 to 4, in a case where each of k, m, and n is 2 or more, a plurality of R3's, R4's, or R5's may be the same or different from each other, A is a group represented by —S—, —O—, —SO—, —SO$_2$—, or —CO—, 0 is an oxygen atom, S is a sulfur atom, and X$^-$ represents a monovalent polyatomic anion].

A second aspect of the present invention is a pattern formation method including: a step of forming a photosensitive resin film on a support using the negative photosensitive resin composition according to the first aspect; a step of exposing the photosensitive resin film; and a step of developing the exposed photosensitive resin film with a developing solution containing an organic solvent to form a negative pattern.

A third aspect of the present invention is a laminated film obtained by laminating a photosensitive resin composition layer composed of the negative photosensitive resin composition according to the first aspect and a support film.

Advantageous Effects of Invention

According to the present invention, it is possible to provide a negative photosensitive resin composition having higher resolution, a pattern formation method using the same, and a laminated film using the negative photosensitive resin composition.

DESCRIPTION OF EMBODIMENTS

In the present specification and claims, a term "aliphatic" is a relative concept used with respect to a term "aromatic" and defines a group which no aromaticity, a compound with no aromaticity, or the like.

A term "alkyl group" includes linear, branched, or cyclic monovalent saturated hydrocarbon groups unless otherwise specified. The same applies to an alkyl group in an alkoxy group.

A term "alkylene group" includes linear, branched, or cyclic divalent saturated hydrocarbon groups unless otherwise specified.

A "halogenated alkyl group" is a group in which a part of or all hydrogen atoms in an alkyl group are substituted with halogen atoms. As the halogen atom, a fluorine atom, a chlorine atom, a bromine atom, and an iodine atom are exemplary examples.

A "fluorinated alkyl group" refers to a group in which a part of or all hydrogen atoms in an alkyl group are substituted with fluorine atoms.

A term "constitutional unit" indicates a monomer unit constituting a polymer compound (a resin, a polymer, or a copolymer).

An expression "may have a substituent" includes a case where a hydrogen atom (—H) is substituted with a monovalent group and a case where a methylene group (—CH$_2$—) is substituted with a divalent group.

A term "exposure" is used as a general concept for irradiation with radiation.

(Negative Photosensitive Resin)

A negative photosensitive resin composition (hereinafter, may be simply referred to as a "photosensitive composition") according to the present embodiment contains an epoxy group-containing resin (A) and a cationic polymerization initiator (I). Hereinafter, each of these components is also referred to as a component (A) and a component (I).

In a case where a photosensitive resin film is formed of such a photosensitive composition and selective exposure is performed on the photosensitive resin film, since a cation moiety of the component (I) is decomposed to generate an acid in an exposed portion of the photosensitive resin film, and an epoxy group in the component (A) is subjected to ring-opening polymerization due to an action of the acid so that solubility of the component (A) in a developing solution containing an organic solvent is decreased while the solubility of the component (A) in the developing solution containing an organic solvent is not changed in an unexposed portion of the photosensitive resin film. Therefore, a difference in solubility in the developing solution containing an organic solvent occurs between the exposed portion of the photosensitive resin film and the unexposed portion of the photosensitive resin film. Accordingly, in a case where the photosensitive resin film is developed with the developing solution containing an organic solvent, the unexposed portion is dissolved and removed so that a negative pattern is formed.

<Epoxy Group-Containing Resin (A)>

The epoxy group-containing resin (component (A)) is not particularly limited as long as the resin has, in one molecule, an epoxy group sufficient enough to form a pattern by exposure.

As the component (A), for example, a resin having a glycidyl ether group in its structure can be used.

In addition, as the component (A), a novolak-type epoxy resin (Anv), a bisphenol A-type epoxy resin (Abp), a bisphenol F-type epoxy resin, an aliphatic epoxy resin, and an acrylic resin (Aac) are exemplary examples.

<<Novolak-Type Epoxy Resin (any)>>

As the novolak-type epoxy resin (Anv), a resin (A1) (hereinafter, also referred to as a "component (A1)") represented by General Formula (A1) is a suitable exemplary example.

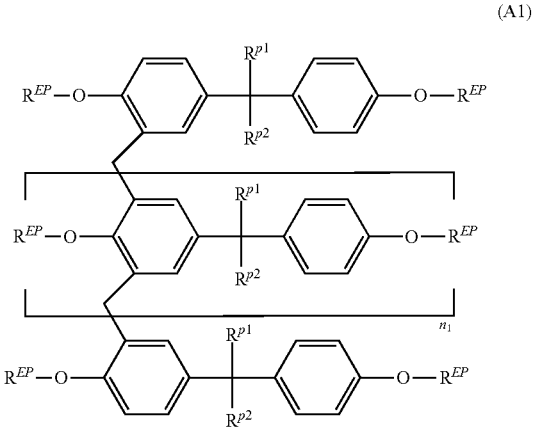

(A1)

[in the formula, $R^{p1}$ and $R^{p2}$ are each independently a hydrogen atom or an alkyl group having 1 to 5 carbon atoms, a plurality of $R^{p1}$'s may be the same or different from each other, a plurality of $R^{p2}$'s may be the same or different from each other, $n_1$ is an integer of 1 to 5, $R^{EP}$ is an epoxy group-containing group, and a plurality of $R^{EP}$'s may be the same or different from each other]

In Formula (A1), the alkyl group having 1 to 5 carbon atoms as $R^{p1}$ and $R^{p2}$ is, for example, a linear, branched, or cyclic alkyl group having 1 to 5 carbon atoms. As the linear or branched alkyl group, a methyl group, an ethyl group, a propyl group, an isopropyl group, an n-butyl group, an isobutyl group, a tert-butyl group, a pentyl group, an isopentyl group, and a neopentyl group are exemplary examples. Further, as the cyclic alkyl group, a cyclobutyl group and a cyclopentyl group are exemplary examples.

Among these, $R^{p1}$ and $R^{p2}$ are preferably a hydrogen atom or a linear or branched alkyl group, more preferably a hydrogen atom or a linear alkyl group, and particularly preferably a hydrogen atom or a methyl group.

In Formula (A1), a plurality of $R^{p1}$'s may be the same or different from each other. A plurality of $R^{p2}$'s may be the same or different from each other.

In Formula (A1), $n_1$ is an integer of 1 to 5, preferably 2 or 3 and more preferably 2.

In Formula (A1), $R^{EP}$ is an epoxy group-containing group.

The epoxy group-containing group as $R^{EP}$ is not particularly limited, and a group consisting of only an epoxy group; a group consisting of only an alicyclic epoxy group; and a group having an epoxy group or an alicyclic epoxy group and a divalent linking group are exemplary examples.

The alicyclic epoxy group is an alicyclic group having an oxacyclopropane structure as a 3-membered ring ether. Specifically, the alicyclic epoxy group is a group having an alicyclic group and an oxacyclopropane structure.

An alicyclic group which is a basic skeleton of the alicyclic epoxy group may be monocyclic or polycyclic. As the monocyclic alicyclic group, a cyclopropyl group, a cyclobutyl group, a cyclopentyl group, a cyclohexyl group, a cycloheptyl group, and a cyclooctyl group are exemplary examples. Further, as the polycyclic alicyclic group, a norbornyl group, an isobornyl group, a tricyclononyl group, a tricyclodecyl group, and a tetracyclododecyl group are exemplary examples. Further, hydrogen atoms in these alicyclic groups may be substituted with an alkyl group, an alkoxy group, a hydroxyl group, or the like.

In a case of the group having an epoxy group or an alicyclic epoxy group and a divalent linking group, it is preferable that the epoxy group or the alicyclic epoxy group is bonded through a divalent linking group bonded to an oxygen atom (—O—) in the formula.

Here, the divalent linking group is not particularly limited, and a divalent hydrocarbon group which may have a substituent and a divalent linking group including a hetero atom are suitable exemplary examples.

Regarding the divalent hydrocarbon group which may have a substituent:

such a divalent hydrocarbon group may be an aliphatic hydrocarbon group or an aromatic hydrocarbon group; and the aliphatic hydrocarbon group in the divalent hydrocarbon group may be saturated or unsaturated, and in general, it is preferable that the aliphatic hydrocarbon group is saturated.

More specifically, as the aliphatic hydrocarbon group, a linear or branched aliphatic hydrocarbon group and an aliphatic hydrocarbon group including a ring in the structure thereof are exemplary examples.

The number of carbon atoms in the above-described linear aliphatic hydrocarbon group is preferably 1 to 10, more preferably 1 to 6, still more preferably 1 to 4, and most preferably 1 to 3. As the linear aliphatic hydrocarbon group, a linear alkylene group is preferable. Specifically, a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—] are exemplary examples.

The number of carbon atoms in the above-described branched aliphatic hydrocarbon group is preferably 2 to 10, more preferably 2 to 6, still more preferably 2 to 4, and most preferably 2 to 3. As the branched aliphatic hydrocarbon group, a branched alkylene group is preferable. Specifically, alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$— and —$CH_2CH(CH_3)CH_2CH_2$— are exemplary examples. As an alkyl group in the alkylalkylene group, a linear alkyl group having 1 to 5 carbon atoms is preferable.

As the aliphatic hydrocarbon group including a ring in the structure thereof, an alicyclic hydrocarbon group (a group formed by removing two hydrogen atoms from an aliphatic hydrocarbon ring), a group in which an alicyclic hydrocarbon group is bonded to the terminal of a linear or branched aliphatic hydrocarbon group, and a group in which an alicyclic hydrocarbon group is interposed in a linear or branched aliphatic hydrocarbon group are exemplary examples. As the linear or branched aliphatic hydrocarbon group, the same as those described above is an exemplary example.

The number of carbon atoms in the alicyclic hydrocarbon group is preferably 3 to 20 and more preferably 3 to 12.

The alicyclic hydrocarbon group may be a polycyclic group or a monocyclic group. As the monocyclic alicyclic hydrocarbon group, a group formed by removing two hydrogen atoms from a monocycloalkane is preferable. The number of carbon atoms in the monocycloalkane is preferably 3 to 6, and specifically, cyclopentane and cyclohexane are exemplary examples.

As the polycyclic alicyclic hydrocarbon group, a group formed by removing two hydrogen atoms from a polycycloalkane is preferable. The number of carbon atoms in the polycycloalkane is preferably 7 to 12, and specifically, adamantane, norbornane, isobornane, tricyclodecane, and tetracyclododecane are exemplary examples.

The aromatic hydrocarbon group in the divalent hydrocarbon group is a hydrocarbon group having at least one aromatic ring. The aromatic ring is not particularly limited as long as the aromatic ring has a cyclic conjugated system having (4n+2) pieces of 1 electrons, and may be monocyclic or polycyclic. The number of carbon atoms in the aromatic ring is preferably 5 to 30, more preferably 5 to 20, still more preferably 6 to 15, and particularly preferably 6 to 12. Specifically, as the aromatic ring, an aromatic hydrocarbon ring such as benzene, naphthalene, anthracene, and phenanthrene; and an aromatic heterocyclic ring in which a part of carbon atoms constituting the aromatic hydrocarbon ring are substituted with hetero atoms are exemplary examples. As the hetero atom in the aromatic heterocyclic ring, an oxygen atom, a sulfur atom, and a nitrogen atom are exemplary examples. Specifically, as the aromatic heterocyclic ring, a pyridine ring and a thiophene ring are exemplary examples.

Specifically, as the aromatic hydrocarbon group, a group (an arylene group or a heteroarylene group) formed by removing two hydrogen atoms from the aromatic hydrocarbon ring or the aromatic heterocyclic ring; a group formed by removing two hydrogen atoms from an aromatic compound (biphenyl, fluorene, or the like) having two or more aromatic rings; and a group (a group in which one hydrogen atom is further removed from an aryl group in an arylalkyl group such as a benzyl group, a phenethyl group, a 1-naphthylmethyl group, a 2-naphthylmethyl group, a 1-naphthylethyl group, and a 2-naphthylethyl group) in which one hydrogen atom of a group (an aryl group or a heteroaryl group) formed by removing one hydrogen atom from the aromatic hydrocarbon ring or the aromatic heterocyclic ring is substituted with an alkylene group are exemplary examples. The number of carbon atoms in the alkylene group which is bonded to the above-described aryl group or heteroaryl group is preferably 1 to 4, more preferably 1 or 2, and particularly preferably 1.

The divalent hydrocarbon group may have a substituent.

The linear or branched aliphatic hydrocarbon group as the divalent hydrocarbon group may or may not have a substituent. As the substituent, a fluorine atom, a fluorinated alkyl group having 1 to 5 carbon atoms which is substituted with a fluorine atom, and a carbonyl group are exemplary examples.

The alicyclic hydrocarbon group in the aliphatic hydrocarbon group including a ring in the structure thereof, as the divalent hydrocarbon group, may or may not have a substituent. As the substituent, an alkyl group, an alkoxy group, a halogen atom, a halogenated alkyl group, a hydroxyl group, and a carbonyl group are exemplary examples.

As the alkyl group as the above-described substituent, an alkyl group having 1 to 5 carbon atoms is preferable, and a methyl group, an ethyl group, a propyl group, an n-butyl group, or a tert-butyl group is most preferable.

As the alkoxy group as the above-described substituent, an alkoxy group having 1 to 5 carbon atoms is preferable, a methoxy group, an ethoxy group, an n-propoxy group, an iso-propoxy group, an n-butoxy group, or a tert-butoxy group is preferable, and a methoxy group or an ethoxy group is most preferable.

As the halogen atom as the above-described substituent, a fluorine atom, a chlorine atom, a bromine atom, and an iodine atom are exemplary examples. Among these, a fluorine atom is preferable.

As the halogenated alkyl group as the above-described substituent, a group in which a part of or all hydrogen atoms in the alkyl group are substituted with the halogen atoms is an exemplary example.

In the alicyclic hydrocarbon group, a part of carbon atoms constituting the ring structure thereof may be substituted with substituents having a hetero atom. As the substituent having a hetero atom, —O—, —C(=O)—O—, —S—, —S(=O)$_2$—, or —S(=O)$_2$—O— is preferable.

In the aromatic hydrocarbon group as the divalent hydrocarbon group, a hydrogen atom in the aromatic hydrocarbon group may be substituted with a substituent. For example, the hydrogen atom bonded to the aromatic ring in the aromatic hydrocarbon group may be substituted with a substituent. As the substituent, an alkyl group, an alkoxy group, a halogen atom, a halogenated alkyl group, and a hydroxyl group are exemplary examples.

As the alkyl group as the above-described substituent, an alkyl group having 1 to 5 carbon atoms is preferable, and a methyl group, an ethyl group, a propyl group, an n-butyl group, or a tert-butyl group is most preferable.

As the alkoxy group, the halogen atom, and the halogenated alkyl group as the above-described substituent, the same as exemplary examples of the substituent which substitutes the hydrogen atom in the alicyclic hydrocarbon group is an exemplary example.

Regarding divalent linking group including hetero atom:

the hetero atom in the divalent linking group including a hetero atom is an atom other than a carbon atom and a hydrogen atom, and an oxygen atom, a nitrogen atom, a sulfur atom, and a halogen atom are exemplary examples.

In the divalent linking group including a hetero atom, as the linking group, —O—, —C(=O)—O—, —C(=O)—, —O—C(=O)—O—; —C(=O)—NH—, —NH—, —NH—C(=O)—O—, —NH—C(=NH)— (H may be substituted with a substituent such as an alkyl group, an acyl group, and the like); —S—, —S(=O)$_2$—, —S(=O)$_2$—O—, and a group represented by General Formulae —Y$^{21}$—O—Y$^{22}$—, —Y$^{21}$—, —Y$^{21}$—C(=O)—O—, —C(=O)—O—Y$^{21}$—[Y$^{21}$—C(=O)—O]$_{m''}$—Y$^{22}$—, or —Y$^{21}$—O—C(=O)—Y$^{22}$— [in the formulae, Y$^{21}$ and Y$^{22}$ each independently represent a divalent hydrocarbon group which may have a substituent, O represents an oxygen atom, and m'' represents an integer of 0 to 3] are exemplary examples.

In a case where the divalent linking group including a hetero atom is —C(=O)—NH—, —NH—, —NH—C(=O)—O—, or —NH—C(=NH)—, H may be substituted with a substituent such as an alkyl group, an acyl group, and the like. The substituent (alkyl group, acyl group, and the like) preferably has 1 to 10 carbon atoms, more preferably has 1 to 8 carbon atoms, and particularly preferably has 1 to 5 carbon atoms.

In Formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, or —Y$^{21}$—O—C(=O)—Y$^{22}$—, Y$^{21}$ and Y$^{22}$ each independently represent a divalent hydrocarbon group which may have a substituent. As the divalent hydrocarbon group, the same groups as those described above as the "divalent hydrocarbon group which may have a substituent" in the definition of the above-described divalent linking group are exemplary examples.

As Y$^{21}$, a linear aliphatic hydrocarbon group is preferable, a linear alkylene group is more preferable, a linear alkylene group having 1 to 5 carbon atoms is still more preferable, and a methylene group or an ethylene group is particularly preferable.

As Y$^{22}$, a linear or branched aliphatic hydrocarbon group is preferable, and a methylene group, an ethylene group, or an alkylmethylene group is more preferable. The alkyl group in the alkylmethylene group is preferably a linear alkyl group having 1 to 5 carbon atoms, more preferably a linear alkyl group having 1 to 3 carbon atoms, and most preferably a methyl group.

In the group represented by the formula —[Y$^{21}$—C(=O)—O]$_{m''}$—Y$^{22}$—, m'' is an integer of 0 to 3, preferably an integer of 0 to 2, more preferably 0 or 1, and particularly preferably 1. That is, it is particularly preferable that the group represented by Formula —[Y$^{21}$—C(=O)—O]$_{m''}$—Y$^{22}$— is a group represented by Formula —Y$^{21}$—C(=O)—O—Y$^{22}$—. Among these, a group represented by Formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Among these, a glycidyl group is preferable as the epoxy group-containing group in R$^{EP}$.

Further, as the novolak-type epoxy resin (Anv), a resin having a constitutional unit represented by General Formula (anv1) is also a suitable exemplary example.

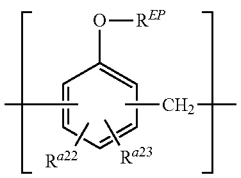

(anv1)

[in the formula, $R^{EP}$ is an epoxy group-containing group, and $R^{a22}$ and $R^{a23}$ are each independently a hydrogen atom, an alkyl group having 1 to 5 carbon atoms, or a halogen atom]

In Formula (anv1), the alkyl group having 1 to 5 carbon atoms as $R^{a22}$ and $R^{a23}$ has the same definition as the alkyl group having 1 to 5 carbon atoms as $R^{p1}$ and $R^{p2}$ in Formula (A1). It is preferable that the halogen atom as $R^{a22}$ and $R^{a23}$ is a chlorine atom or a bromine atom.

In Formula (anv1), $R^{EP}$ has the same definition as that for $R^{EP}$ in Formula (A1), and it is preferable that $R^{EP}$ represents a glycidyl group.

Specific examples of the constitutional unit represented by Formula (anv1) are shown below.

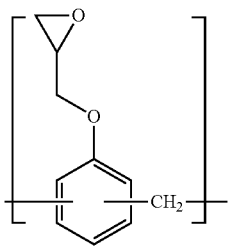

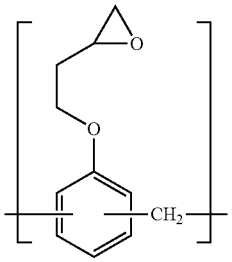

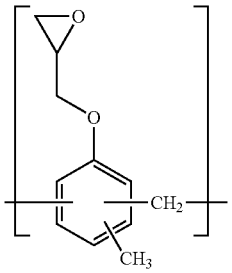

The novolak-type epoxy resin (Anv) may be a resin consisting of only the above-described constitutional unit (anv1) or a resin having the constitutional unit (anv1) and other constitutional units. As the other constitutional units, constitutional units represented by General Formulae (anv2) and (anv3) are exemplary examples.

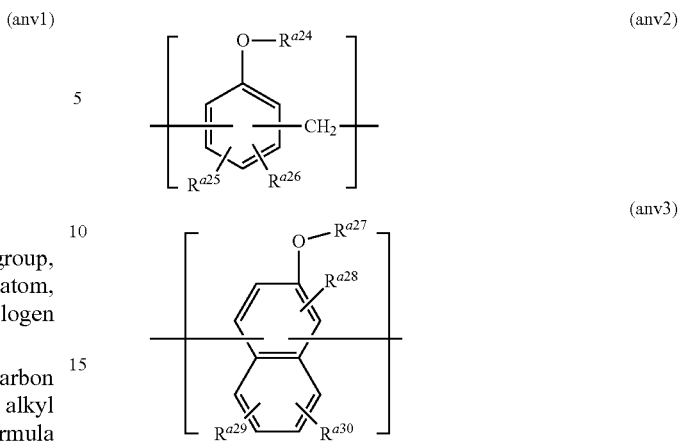

[in the formulae, $R^{a24}$ is a hydrocarbon group which may have a substituent, $R^{a25}$, $R^{a26}$, and $R^{a28}$ to $R^{a30}$ are each independently a hydrogen atom, an alkyl group having 1 to 5 carbon atoms, or a halogen atom, and $R^{a27}$ is an epoxy group-containing group or a hydrocarbon group which may have a substituent]

In Formula (anv2), $R^{a24}$ is a hydrocarbon group which may have a substituent. As the hydrocarbon group which may have a substituent, a linear or branched alkyl group and a cyclic hydrocarbon group are exemplary examples.

The linear alkyl group preferably has 1 to 5 carbon atoms, more preferably has 1 to 4 carbon atoms, and still more preferably has 1 or 2 carbon atoms. Specifically, a methyl group, an ethyl group, an n-propyl group, an n-butyl group, and an n-pentyl group are exemplary examples. Among these, a methyl group, an ethyl group, or an n-butyl group is preferable, and a methyl group or an ethyl group is more preferable.

The branched alkyl group preferably has 3 to 10 carbon atoms and more preferably has 3 to 5 carbon atoms. Specifically, an isopropyl group, an isobutyl group, a tert-butyl group, an isopentyl group, a neopentyl group, an 1,1-diethylpropyl group, and a 2,2-dimethylbutyl group are exemplary examples. Among these, an isopropyl group is preferable.

In a case where $R^{a24}$ is a cyclic hydrocarbon group, the cyclic hydrocarbon group may be an aliphatic hydrocarbon group or an aromatic hydrocarbon group, and may be a polycyclic group or a monocyclic group.

As the aliphatic hydrocarbon group which is a monocyclic group, a group formed by removing one hydrogen atom from a monocycloalkane is preferable. The number of carbon atoms in the monocycloalkane is preferably 3 to 6, and specifically, cyclopentane and cyclohexane are exemplary examples.

As the aliphatic hydrocarbon group which is a polycyclic group, a group formed by removing one hydrogen atom from a polycycloalkane is preferable. The number of carbon atoms in the polycycloalkane is preferably 7 to 12, and specifically, adamantane, norbornane, isobornane, tricyclodecane, and tetracyclododecane are exemplary examples.

In a case where the cyclic hydrocarbon group as $R^{a24}$ is an aromatic hydrocarbon group, the aromatic hydrocarbon group is a hydrocarbon group having at least one aromatic ring.

The aromatic ring is not particularly limited as long as the aromatic ring has a cyclic conjugated system having (4n+2) pieces of a electrons, and may be monocyclic or polycyclic.

The number of carbon atoms in the aromatic ring is preferably 5 to 30, more preferably 5 to 20, still more preferably 6 to 15, and particularly preferably 6 to 12. Specifically, as the aromatic ring, an aromatic hydrocarbon ring such as benzene, naphthalene, anthracene, and phenanthrene; and an aromatic heterocyclic ring in which a part of carbon atoms constituting the aromatic hydrocarbon ring are substituted with hetero atoms are exemplary examples. As the hetero atom in the aromatic heterocyclic ring, an oxygen atom, a sulfur atom, and a nitrogen atom are exemplary examples. Specifically, as the aromatic heterocyclic ring, a pyridine ring and a thiophene ring are exemplary examples.

Specifically, as the aromatic hydrocarbon group in $R^{a24}$, a group (an aryl group or a heteroaryl group) formed by removing one hydrogen atom from the aromatic hydrocarbon ring or aromatic heterocyclic ring; a group formed by removing one hydrogen atom from an aromatic compound (biphenyl, fluorene, or the like) having two or more aromatic rings; and a group (for example, an arylalkyl group such as a benzyl group, a phenethyl group, a 1-naphthylmethyl group, a 2-naphthylmethyl group, a 1-naphthylethyl group, and a 2-naphthylethyl group) in which one hydrogen atom in an aromatic hydrocarbon ring or aromatic heterocyclic ring is substituted with an alkylene group are exemplary examples. The number of carbon atoms in the alkylene group which is bonded to the aromatic hydrocarbon ring or the aromatic heterocyclic ring is preferably 1 to 4, more preferably 1 or 2, and particularly preferably 1.

In Formulae (anv2) and (anv3), $R^{a25}$ and $R^{a26}$, and $R^{a28}$ to $R^{a30}$ are each independently a hydrogen atom, an alkyl group having 1 to 5 carbon atoms, or a halogen atom, and the alkyl group having 1 to 5 carbon atoms and the halogen atom each have the same definition as that for $R^{a22}$ and $R^{a23}$ In Formula (anv3), $R^{a27}$ is an epoxy group-containing group or a hydrocarbon group which may have a substituent. The epoxy group-containing group as $R^{a27}$ has the same definition as that for $R^{EP}$ in Formula (A1), and the hydrocarbon group which may have a substituent as $R^{a27}$ has the same definition as that for $R^{a24}$ Specific examples of the constitutional units represented by Formulae (anv2) and (anv3) are shown below.

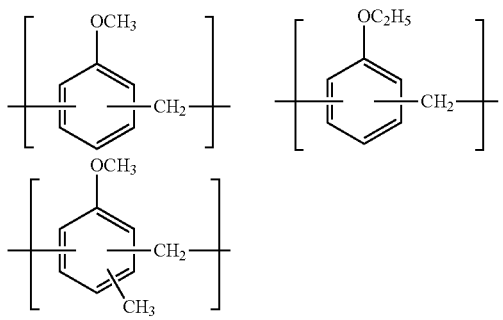

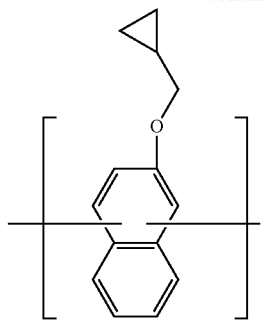

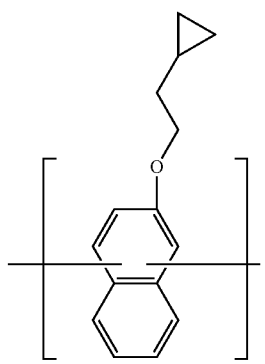

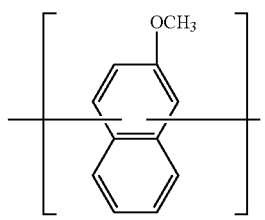

In a case where the novolak-type epoxy resin (Anv) has other constitutional units in addition to the constitutional unit (anv1), a proportion of each constitutional unit in the resin (Anv) is not particularly limited, but the total amount of the constitutional units having an epoxy group is preferably 10 to 90 mol %, more preferably 20 to 80 mol %, and still more preferably 30 to 70 mol % with respect to the total amount of all constitutional units constituting the resin (Anv).

<<Bisphenol A-Type Epoxy Resin (Abp)>>

As the bisphenol A-type epoxy resin (Abp), an epoxy resin having a structure represented by General Formula (abp1) is an exemplary example.

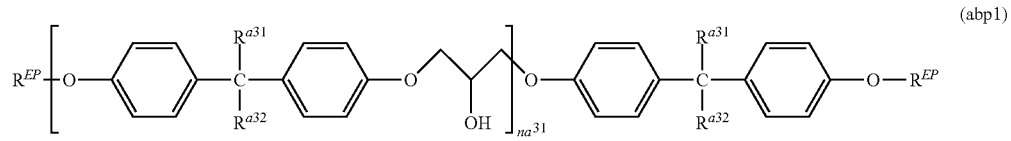

[in the formula, $R^{EP}$ is an epoxy group-containing group, $R^{a31}$ and $R^{a32}$ are each independently a hydrogen atom or an alkyl group having 1 to 5 carbon atoms, and $na^{31}$ is an integer of 1 to 50]

In Formula (abp1), the alkyl group having 1 to 5 carbon atoms for $R^{a31}$ and $R^{a32}$ has the same definition as that for $R^{p1}$ and $R^{p2}$ in Formula (A1). Among these, it is preferable that $R^{a31}$ and $R^{a32}$ are a hydrogen atom or a methyl group.

$R^{EP}$ has the same definition as that for $R^{EP}$ in Formula (A1), and it is preferable that $R^{EP}$ represents a glycidyl group.

<<Aliphatic Epoxy Resin and Acrylic Resin (Aac)>>

As the aliphatic epoxy resin and the acrylic resin (Aac), resins having an epoxy group-containing unit represented by General Formulae (a1-1) and (a1-2) are exemplary examples.

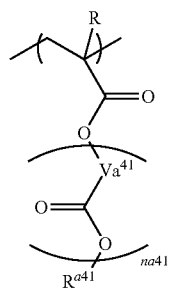

(a1-1)

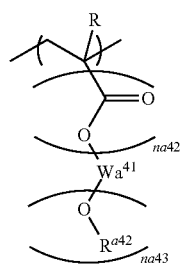

(a1-2)

[in the formulae, R is a hydrogen atom, an alkyl group having 1 to 5 carbon atoms, or a halogenated alkyl group having 1 to 5 carbon atoms, $Va^{41}$ is a divalent hydrocarbon group which may have a substituent, $na^{41}$ is an integer of 0 to 2, $R^{a41}$ and $R^{a42}$ are an epoxy group-containing group, $na^{42}$ is 0 or 1, $Wa^{41}$ is an $(na^{43}+1)$-valent aliphatic hydrocarbon group, and $na^{43}$ is an integer of 1 to 3]

In Formula (a1-1), R is a hydrogen atom, an alkyl group having 1 to 5 carbon atoms, or a halogenated alkyl group having 1 to 5 carbon atoms.

As the alkyl group having 1 to 5 carbon atoms as R, a linear or branched alkyl group is preferable, and specifically, a methyl group, an ethyl group, a propyl group, an isopropyl group, an n-butyl group, an isobutyl group, a tert-butyl group, a pentyl group, an isopentyl group, and a neopentyl group are exemplary examples.

The halogenated alkyl group having 1 to 5 carbon atoms as R is a group in which a part of or all hydrogen atoms in the alkyl group having 1 to 5 carbon atoms are substituted with halogen atoms. As the halogen atom include a fluorine atom, a chlorine atom, a bromine atom, and an iodine atom are exemplary examples. Among these, a fluorine atom is particularly preferable.

As R, a hydrogen atom, an alkyl group having 1 to 5 carbon atoms, or a fluorinated alkyl group having 1 to 5 carbon atoms is preferable, and a hydrogen atom or a methyl group is most preferable from the viewpoint of industrial availability.

In Formula (a1-1), $Va^{41}$ is a divalent hydrocarbon group which may have a substituent, and the same groups as those for the divalent hydrocarbon group which may have a substituent, described in the section of $R^{EP}$ in Formula (A1), are exemplary examples.

Among these, as the hydrocarbon group represented by $Va^{41}$, an aliphatic hydrocarbon group is preferable, a linear or branched aliphatic hydrocarbon group is more preferable, a linear aliphatic hydrocarbon group is still more preferable, and a linear alkylene group is particularly preferable.

In Formula (a1-1), $na^{41}$ is an integer of 0 to 2, preferably 0 or 1.

In Formulae (a1-1) and (a1-2), $R^{a41}$ and $R^{a42}$ are an epoxy group-containing group and have the same definition as that for $R^{EP}$ in Formula (A1).

In Formula (a1-2), the $(na^{43}+1)$-valent aliphatic hydrocarbon group in $Wa^{41}$ indicates a hydrocarbon group with no aromaticity, and may be saturated or unsaturated. In general, it is preferable that the aliphatic hydrocarbon group is saturated. As the above-described aliphatic hydrocarbon group, a linear or branched aliphatic hydrocarbon group, an aliphatic hydrocarbon group having a ring in the structure thereof, and a group formed by combining a linear or branched aliphatic hydrocarbon group and an aliphatic hydrocarbon group having a ring in the structure thereof are exemplary examples.

In Formula (a1-2), $na^{43}$ is an integer of 1 to 3, preferably 1 or 2.

Specific examples of the constitutional unit represented by Formula (a1-1) or (a1-2) are shown below.

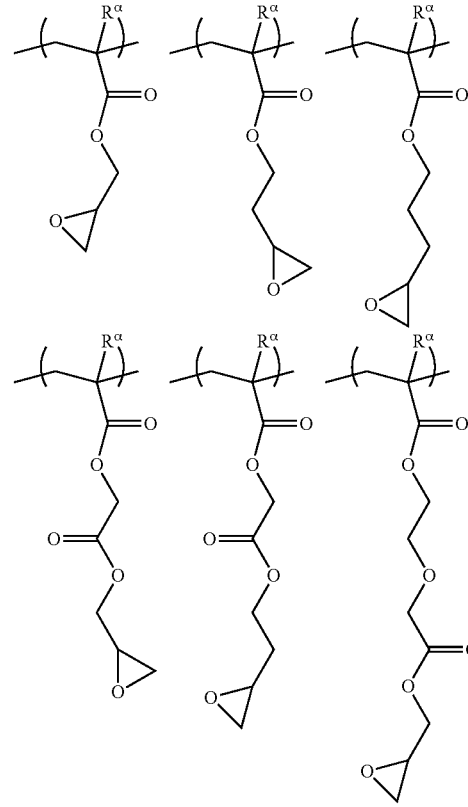

-continued
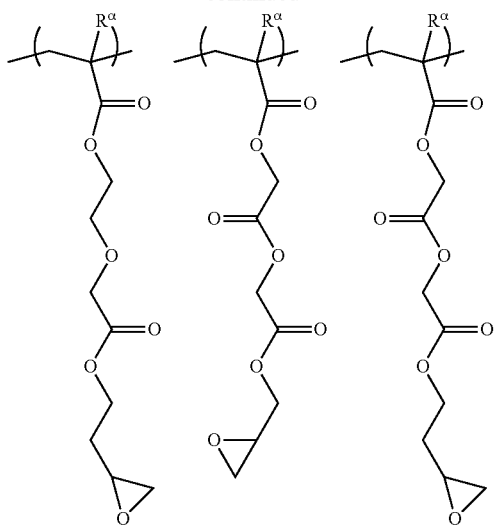
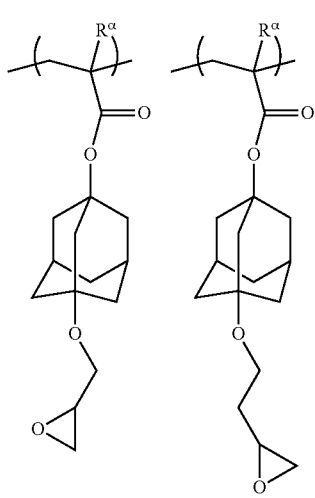
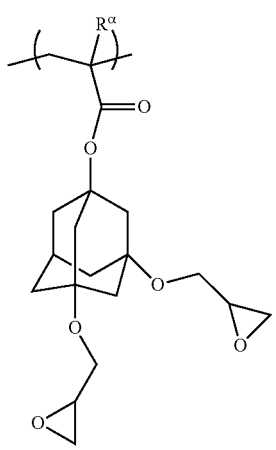
-continued
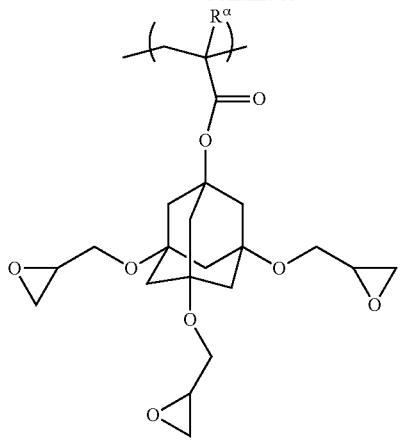
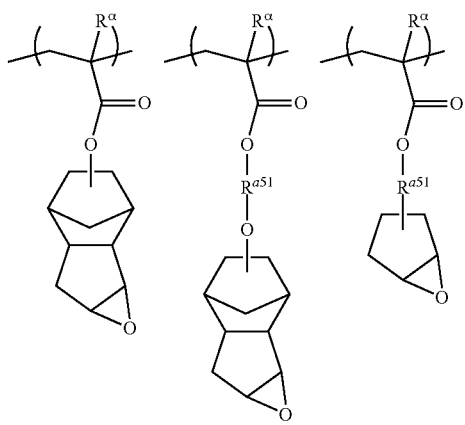
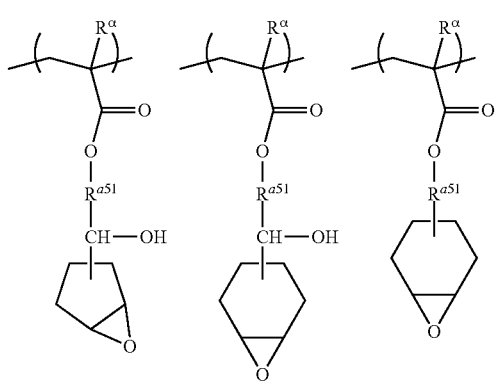

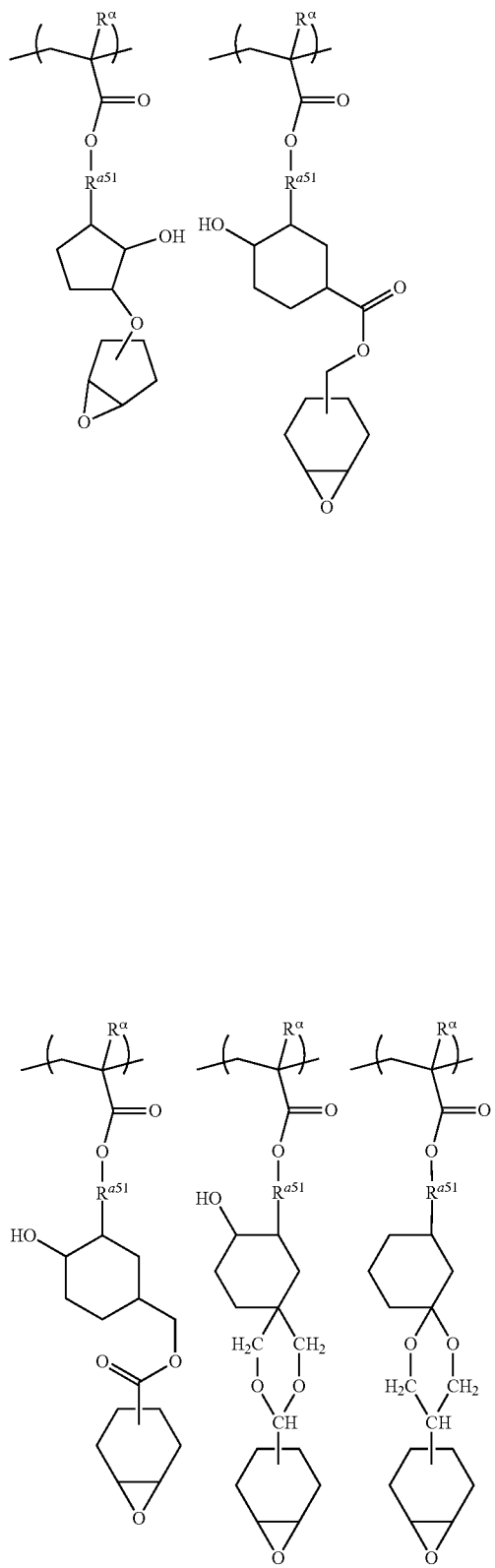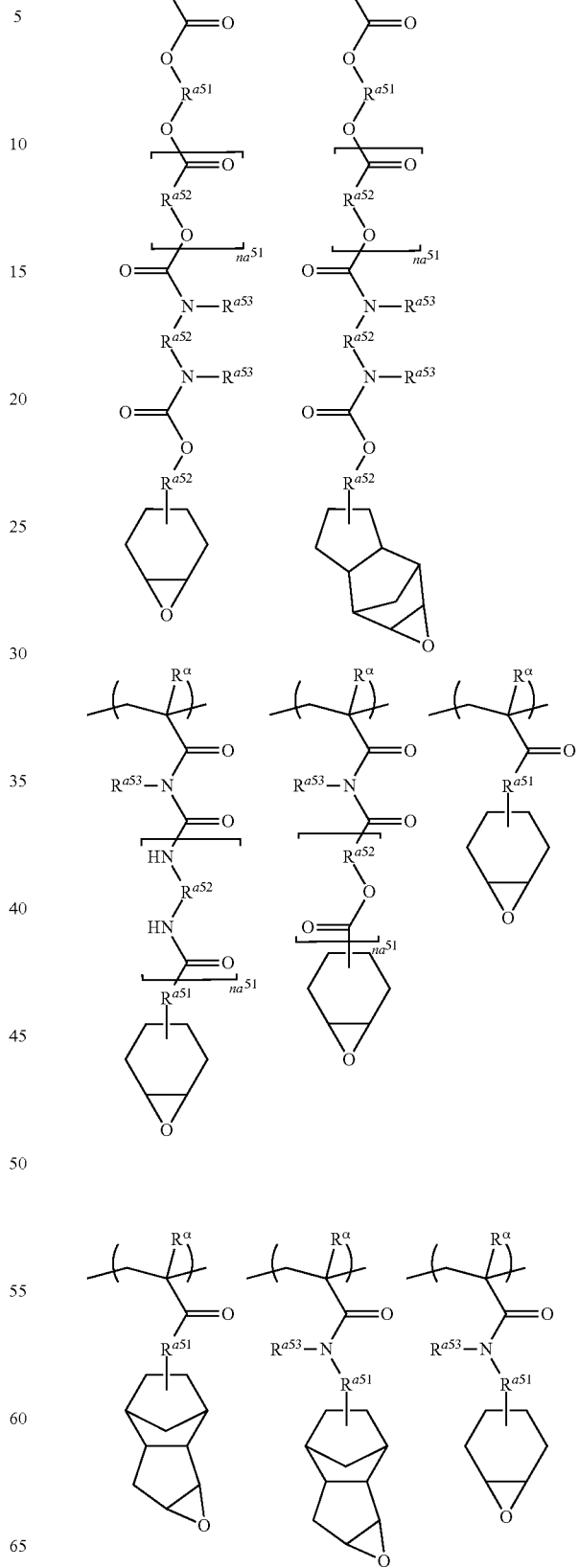

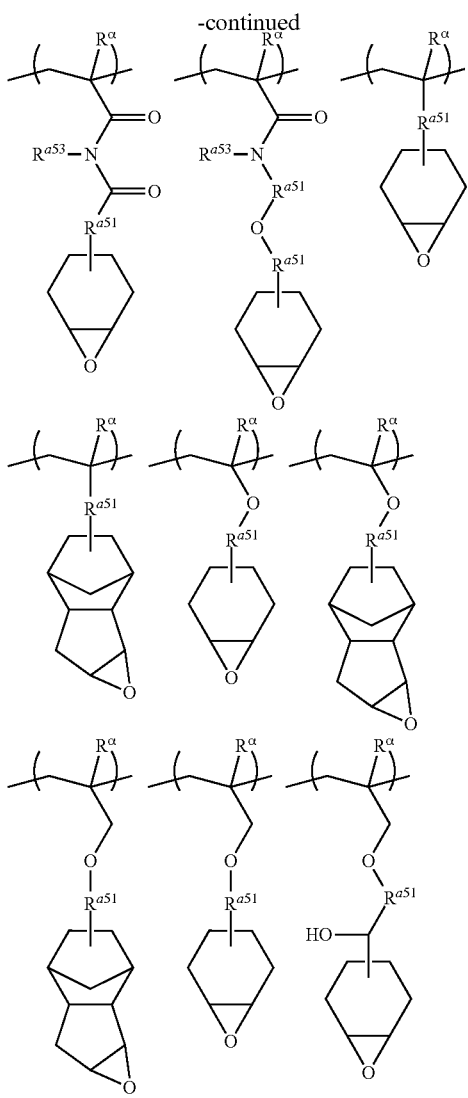

In the formulae, $R^a$ represents a hydrogen atom, a methyl group, or a trifluoromethyl group.

$R^{a51}$ represents a divalent hydrocarbon group having 1 to 8 carbon atoms. $R^{a52}$ represents a divalent hydrocarbon group having 1 to 20 carbon atoms. $R^{a53}$ represents a hydrogen atom or a methyl group. $na^{51}$ is an integer of 0 to 10.

$R^{a51}$, $R^{a52}$, and $R^{a53}$ may be the same or different from each other.

Further, the acrylic resin (Aac) may have a constitutional unit derived from other polymerizable compounds for the purpose of appropriately controlling physical and chemical characteristics. As such a polymerizable compound, known radical polymerizable compounds and anionic polymerizable compounds are exemplary examples. As such a polymerizable compound, monocarboxylic acids such as acrylic acid, methacrylic acid, and crotonic acid; dicarboxylic acids such as maleic acid, fumaric acid, and itaconic acid; methacrylic acid derivatives containing a carboxyl group and an ester bond such as 2-methacryloyloxyethyl succinic acid, 2-methacryloyloxyethyl maleic acid, 2-methacryloyloxyethyl phthalic acid, and 2-methacryloyloxyethyl hexahydrophthalic acid; (meth)acrylic acid alkyl esters such as methyl (meth)acrylate, ethyl (meth)acrylate, and butyl (meth)acrylate; (meth)acrylic acid hydroxy alkyl esters such as 2-hydroxyethyl (meth)acrylate and 2-hydroxypropyl (meth)acrylate; (meth)acrylic acid aryl esters such as phenyl (meth)acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene, and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; and amide bond-containing polymerizable compounds such as acrylamide and methacrylamide are exemplary examples.

In a case where the aliphatic epoxy resin and the acrylic resin (Aac) have other constitutional units, a content ratio of the epoxy group-containing unit in the resin is preferably 5 to 40 mol %, more preferably 10 to 30 mol %, and most preferably 15 to 25 mol %.

Further, as the aliphatic epoxy resin, a compound (hereinafter, also referred to as a "component (m1)") having a partial structure represented by General Formula (m1) is also a suitable exemplary example.

(m1)

[in the formula, $n_2$ is an integer of 1 to 4, and * represents a bonding site]

In Formula (m1), $n_2$ is an integer of 1 to 4, preferably an integer of 1 to 3 and more preferably 2.

As the component (m1), compounds in which a plurality of the partial structures represented by General Formula (m1) described above are bonded through a divalent linking group or a single bond are exemplary examples. Among these, a compound in which a plurality of the partial structures represented by General Formula (m1) described above are bonded through a divalent linking group is preferable.

Here, the divalent linking group is not particularly limited, and a divalent hydrocarbon group which may have a substituent and a divalent linking group including a hetero atom is a suitable exemplary example. The divalent hydrocarbon group which may have a substituent and the divalent linking group including a hetero atom are the same as the divalent hydrocarbon group which may have a substituent and the divalent linking group including a hetero atom, described in $R^{EP}$ (epoxy group-containing group) in Formula (A1) described above. Among these, the divalent linking group including a hetero atom is preferable, and a group represented by —$Y^{21}$-C(=O)—O— or a group represented by —C(=O)—O—$Y^{21}$— is more preferable. As $Y^{21}$, a linear aliphatic hydrocarbon group is preferable, a linear alkylene group is more preferable, a linear alkylene group having 1 to 5 carbon atoms is still more preferable, and a methylene group or an ethylene group is particularly preferable.

Furthermore, as the aliphatic epoxy resin, a compound (hereinafter, also referred to as a "component (m2)") represented by General Formula (m2) is also a suitable exemplary example.

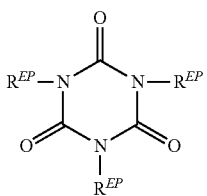

(m2)

[in the formula, $R^{EP}$ is an epoxy group-containing group, and a plurality of $R^{EP}$'s may be the same or different from each other]

In Formula (m2), $R^{EP}$ is an epoxy group-containing group and has the same definition as that for $R^{EP}$ in Formula (A1).

The component (A) may be used alone or in combination of two or more kinds thereof.

As the component (A), it is preferable to use a resin having a glycidyl ether group in its structure.

It is preferable that the component (A) includes at least one resin selected from the group consisting of the novolak-type epoxy resin (Anv), the bisphenol A-type epoxy resin (Abp), the bisphenol F-type epoxy resin, the aliphatic epoxy resin, and the acrylic resin (Aac).

Among these, it is more preferable that the component (A) includes at least one resin selected from the group consisting of the novolak-type epoxy resin (Anv) and the bisphenol A-type resin (Abp).

Among these, it is still more preferable that the component (A) includes both the novolak-type epoxy resin (Anv) and the bisphenol A-type resin (Abp), and it is particularly preferable that the component (A) includes the resin (A1) represented by General Formula (A1) described above and the epoxy resin represented by General Formula (abp1) described above.

In a case where both the novolak-type epoxy resin (Anv) and the bisphenol A-type resin (Abp) are included, a ratio of the novolak-type epoxy resin (Anv) and the bisphenol A-type resin (Abp) is, as a mass ratio represented by component (Anv)/component (Abp), preferably 5/95 to 50/50, more preferably 10/90 to 40/60, and still more preferably 10/90 to 30/70.

In a case where the mass ratio is within the above-described preferred range, resolution is further enhanced and adhesion to a substrate is excellent.

In a case where the component (A) includes at least one resin selected from the group consisting of the novolak-type epoxy resin (Anv) and the bisphenol A-type resin (Abp), from the viewpoint of balance between hardness and flexibility of a cured film, a content proportion of the novolak-type epoxy resin (Anv) to the component (A) is preferably 5% to 50% by mass and more preferably 10% to 30% by mass with respect to the total mass (100% by mass) of the component (A).

A content proportion of the bisphenol A-type resin (Abp) to the component (A) is preferably 50% to 95% by mass and more preferably 70% to 90% by mass with respect to the total mass (100% by mass) of the component (A).

The total content proportion of the novolak-type epoxy resin (Anv) and the bisphenol A-type resin (Abp) is preferably 50% by mass or more, more preferably 80% by mass or more, still more preferably 90% by mass or more with respect to the total mass (100% by mass) of the component (A), and may be 100% by mass.

A mass-average molecular weight of the component (A) in terms of polystyrene is preferably 100 to 300000, more preferably 200 to 200000, and still more preferably 300 to 200000. By setting the mass-average molecular weight to be within the above-described range, peeling from the support is less likely to occur, and hardness of a cured film to be formed is sufficiently increased.

Further, a dispersity of the component (A) is preferably 1.05 or more. By setting the dispersity thereof to such a value, lithography characteristics in pattern formation are more improved.

The dispersity here indicates a value obtained by dividing the mass-average molecular weight by a number-average molecular weight.

As a commercially available product of the component (A), for example, as the novolak-type epoxy resin (Anv), JER-152, JER-154, JER-157S70, and JER-157S65 (all manufactured by Mitsubishi Chemical Corporation), EPICLON N-740, EPICLON N-770, EPICLON N-775, EPICLON N-660, EPICLON N-665, EPICLON N-670, EPICLON N-673, EPICLON N-680, EPICLON N-690, EPICLON N-695, and EPICLON HP5000 (all manufactured by DIC Corporation), and EOCN-1020 (manufactured by Nippon Kayaku Co., Ltd.) are exemplary examples.

As a commercially available product of the component (A), as the bisphenol A-type epoxy resin (Abp), JER-827, JER-828, JER-834, JER-1001, JER-1002, JER-1003, JER-1055, JER-1007, JER-1009, and JER-1010 (all manufactured by Mitsubishi Chemical Corporation), and EPICLON 860, EPICLON 1050, EPICLON 1051, and EPICLON 1055 (all manufactured by DIC Corporation) are exemplary examples.

As a commercially available product of the component (A), as the bisphenol F-type epoxy resin, JER-806, JER-807, JER-4004, JER-4005, JER-4007, and JER-4010 (all manufactured by Mitsubishi Chemical Corporation), EPICLON830 and EPICLON835 (both manufactured by DIC Corporation), and LCE-21 and RE-602S (both manufactured by Nippon Kayaku Co., Ltd.) are exemplary examples.

As a commercially available product of the component (A), as the aliphatic epoxy resin, ADEKA RESIN EP-4080S, ADEKA RESIN EP-4085S, and ADEKA RESIN EP-4088S (all manufactured by ADEKA CORPORATION), CELLOXIDE 2021P, CELLOXIDE 2081, CELLOXIDE 2083, CELLOXIDE 2085, CELLOXIDE 8000, CELLOXIDE 8010, EHPE-3150, EPOLEAD PB 3600, and EPOLEAD PB4700 (all manufactured by Daicel Corporation), DENACOL EX-211L, EX-212L, EX-214L, EX-216L, EX-321L, and EX-850L (all manufactured by Nagase ChemteX Corporation), and TEPIC-VL (manufactured by Nissan Chemical Industries, Ltd.) are exemplary examples.

A content of the component (A) in the photosensitive composition according to the embodiment may be adjusted according to the film thickness and the like of the photosensitive resin film intended to be formed.

<Cationic Polymerization Initiator (I)>

As the cationic polymerization initiator (component (I)), a compound including a sulfonium salt (I0) (hereinafter, also referred to as a "component (I0)") represented by General Formula (I0) is used.

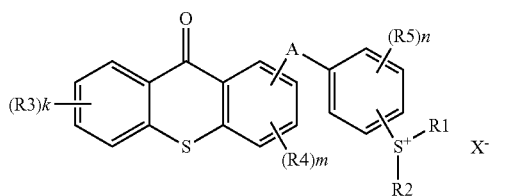

(I0)

[in Formula (I0), R1 and R2 each represent an aryl group having 6 to 30 carbon atoms, a heterocyclic hydrocarbon group having 4 to 30 carbon atoms, or an alkyl group having 1 to 30 carbon atoms, in which a part of hydrogen atoms in the aryl group, the heterocyclic hydrocarbon group, or the alkyl group may be substituted with a substituent (t), the substituent (t) being at least one selected from the group consisting of an alkyl group having 1 to 18 carbon atoms, a hydroxy group, an alkoxy group having 1 to 18 carbon atoms, an alkylcarbonyl group having 2 to 18 carbon atoms, an arylcarbonyl group having 7 to 11 carbon atoms, an acyloxy group having 2 to 19 carbon atoms, an arylthio group having 6 to 20 carbon atoms, an alkylthio group having 1 to 18 carbon atoms, an aryl group having 6 to 10 carbon atoms, a heterocyclic hydrocarbon group having 4 to 20 carbon atoms, an aryloxy group having 6 to 10 carbon atoms, a hydroxy(poly)alkyleneoxy group represented by HO(—$R^A$ O)q- {$R^A$ O represents an ethyleneoxy group and/or a propyleneoxy group and q represents an integer of 1 to 5}, and a halogen atom, R3 to R5 are each an alkyl group, a hydroxy group, an alkoxy group, an alkylcarbonyl group, an arylcarbonyl group, an acyloxy group, an arylthio group, an alkylthio group, an aryl group, a heterocyclic hydrocarbon group, an aryloxy group, a hydroxy(poly)alkyleneoxy group, or a halogen atom, k, m, and n represent the numbers of R3, R4, and R5, in which k is an integer of 0 to 4, m is an integer of 0 to 3, and n is an integer of 1 to 4, in a case where each of k, m, and n is 2 or more, a plurality of R3's, R4's, or R5's may be the same or different from each other, A is a group represented by —S—, —O—, —SO—, —$SO_2$—, or —CO—, 0 is an oxygen atom, S is a sulfur atom, and $X^-$ represents a monovalent polyatomic anion]

<<Component (I0)>>

In R3 to R5 of Formula (I0), as the alkyl group, linear alkyl groups having 1 to 18 carbon atoms (methyl, ethyl, n-propyl, n-butyl, n-pentyl, n-octyl, n-decyl, n-dodecyl, n-tetradecyl, n-hexadecyl, n-octadecyl, and the like), branched alkyl groups having 1 to 18 carbon atoms (isopropyl, isobutyl, sec-butyl, tert-butyl, isopentyl, neopentyl, tert-pentyl, isohexyl, isooctadecyl, and the like), and cycloalkyl groups having 3 to 18 carbon atoms (cyclopropyl, cyclobutyl, cyclopentyl, cyclohexyl, 4-decylcyclohexyl, and the like) are exemplary examples.

In R3 to R5, as the alkoxy group, linear or branched alkoxy groups having 1 to 18 carbon atoms (methoxy, ethoxy, propoxy, isopropoxy, butoxy, isobutoxy, sec-butoxy, tert-butoxy, hexyloxy, decyloxy, dodecyloxy, octadecyloxy, and the like) are exemplary examples.

In R3 to R5, as the alkylcarbonyl group, linear or branched alkylcarbonyl groups having 2 to 18 carbon atoms (acetyl, propionyl, butanoyl, 2-methylpropionyl, heptanoyl, 2-methylbutanoyl, 3-methylbutanoyl, octanoyl, decanoyl, dodecanoyl, octadecanoyl, and the like) are exemplary examples.

In R3 to R5, as the arylcarbonyl group, arylcarbonyl groups having 7 to 11 carbon atoms (benzoyl, naphthoyl, and the like) are exemplary examples.

In R3 to R5, as the acyloxy group, linear or branched acyloxy groups having 2 to 19 carbon atoms (acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy, octadecylcarbonyloxy, and the like) are exemplary examples.

In R3 to R5, as the arylthio group, arylthio groups having 6 to 20 carbon atoms (phenylthio, 2-methylphenylthio, 3-methylphenylthio, 4-methylphenylthio, 2-chlorophenylthio, 3-chlorophenylthio, 4-hlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl] phenylthio, 4-(phenylthio)phenylthio, 4-benzoylphenylthio, 4-benzoyl-2-chlorophenylthio, 4-benzoyl-3-chlorophenylthio, 4-benzoyl-3-methylthiophenylthio, 4-benzoyl-2-methylthiophenylthio, 4-(4-methylthiobenzoyl)phenylthio, 4-(2-methylthiobenzoyl)phenylthio, 4-(p-methylbenzoyl) phenylthio, 4-(p-ethylbenzoyl)phenylthio, 4-(p-isopropylbenzoyl)phenylthio, 4-(p-tert-butylbenzoyl) phenylthio, and the like) are exemplary examples.

In R3 to R5, as the alkylthio group, linear or branched alkylthio groups having 1 to 18 carbon atoms (methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio, isooctadecylthio, and the like) are exemplary examples.

In R3 to R5, as the aryl group, aryl groups having 6 to 10 carbon atoms (phenyl, tolyl, dimethylphenyl, naphthyl, and the like) are exemplary examples.

In R3 to R5, as the heterocyclic hydrocarbon group, heterocyclic hydrocarbon groups having 4 to 20 carbon atoms (thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl, and the like) are exemplary examples.

In R3 to R5, as the aryloxy group, aryloxy groups having 6 to 10 carbon atoms (phenoxy, naphthyloxy, and the like) are exemplary examples.

In R3 to R5, as the hydroxy(poly)alkyleneoxy group, the hydroxy(poly)alkyleneoxy group represented by Formula (2) is an exemplary example.

$$HO(—R^4O)q- \quad (2)$$

$R^4O$ represents an ethyleneoxy group and/or a propyleneoxy group and q represents an integer of 1 to 5.

In R3 to R5, as the halogen atom, a fluorine atom, a chlorine atom, a bromine atom, and an iodine atom are exemplary examples.

R3 to R5 may be the same or different from each other, and may be partially different from each other. In a case where each of k, m, and n described later is 2 or more, a plurality of R3's may be the same or different from each other. A plurality of R4's may be the same or different from each other. A plurality of R5's may be the same or different from each other k represents the number of R3, and is an integer of 0 to 4, preferably 0 to 2, more preferably 0 or 1, and particularly preferably 0.

In addition, m represents the number of R4, and is an integer of 0 to 3, preferably 0 or 1 and particularly preferably 0.

In addition, n represents the number of R5, and is an integer of 1 to 4, preferably 1 or 2 from the viewpoint of availability of industrial raw materials, and particularly preferably 2 from the viewpoint of solubility.

A bonding position of R5 is not limited, but in a case where it is at the ortho position to a C—S' bond, photosensitivity of the sulfonium salt is more improved.

In Formula (I0), A is a group represented by —O—, —S—, —SO—, —SO$_2$—, or —CO—, preferably —S—.

In Formula (I0), R1 and R2 are each selected from an aryl group having 6 to 30 carbon atoms, a heterocyclic hydrocarbon group having 4 to 30 carbon atoms, and an alkyl group having 1 to 30 carbon atoms, in which a part of hydrogen atoms in the aryl group, the heterocyclic hydrocarbon group, or the alkyl group may be substituted with a substituent (t).

The substituent (t) is at least one selected from the group consisting of an alkyl group having 1 to 18 carbon atoms, a hydroxy group, an alkoxy group having 1 to 18 carbon atoms, an alkylcarbonyl group having 2 to 18 carbon atoms, an arylcarbonyl group having 7 to 11 carbon atoms, an acyloxy group having 2 to 19 carbon atoms, an arylthio group having 6 to 20 carbon atoms, an alkylthio group having 1 to 18 carbon atoms, an aryl group having 6 to 10 carbon atoms, a heterocyclic hydrocarbon group having 4 to 20 carbon atoms, an aryloxy group having 6 to 10 carbon atoms, a hydroxy(poly)alkyleneoxy group, and a halogen atom. The substituent (t) has the same definition as the substituent for R3 to R5.

In R1 and R2, the aryl group having 6 to 30 carbon atoms includes a monocyclic aryl group and a condensed polycyclic aryl group.

As the monocyclic aryl group, phenyl, hydroxyphenyl, tolyl, dimethylphenyl, trimethylphenyl, ethylphenyl, diethylphenyl, triethylphenyl, n-propylphenyl, isopropylphenyl, n-butylphenyl, isobutylphenyl, sec-butylphenyl, tert-butylphenyl, methoxyphenyl, ethoxyphenyl, n-propoxyphenyl, isopropoxyphenyl, n-butoxyphenyl, isobutoxyphenyl, sec-butoxyphenyl, tert-butoxyphenyl, acetylphenyl, benzoylphenyl, naphthoylphenyl, phenylthiophenyl, naphthylthiophenyl, biphenylyl, phenoxyphenyl, naphthoxyphenyl, nitrophenyl, fluorophenyl, chlorophenyl, and bromophenyl are exemplary examples.

As the condensed polycyclic aryl group, naphthyl, anthracenyl, phenanthrenyl, pyrenyl, chrysenyl, naphthacenyl, benzanthracenyl, anthraquinolyl, fluorenyl, naphthoquinolyl, hydroxynaphthyl, methylnaphthyl, ethylnaphthyl, methoxynaphthyl, ethoxynaphthyl, acetylnaphthyl, benzoylnaphthyl, phenylthionaphthyl, phenylnaphthyl, phenoxynaphthyl, nitronaphthyl, fluoronaphthyl, chloronaphthyl, bromonaphthyl, hydroxyanthracenyl, methylanthracenyl, ethylanthracenyl, methoxyanthracenyl, ethoxyanthracenyl, acetylanthracenyl, benzoylanthracenyl, phenylthioanthracenyl, phenoxyanthracenyl, nitroanthracenyl, fluoroanthracenyl, chloroanthracenyl, and bromoanthracenyl are exemplary examples.

In R1 and R2, the heterocyclic hydrocarbon group having 4 to 30 carbon atoms includes a cyclic hydrocarbon group including 1 to 3 hetero atoms (an oxygen atom, a nitrogen atom, a sulfur atom, and the like) in the ring, and includes a monocyclic heterocyclic hydrocarbon group and a condensed polycyclic heterocyclic hydrocarbon group.

As the monocyclic heterocyclic hydrocarbon group, thienyl, furanyl, pyranyl, pyrrolyl, oxazolyl, thiazolyl, pyridyl, pyrimidyl, pyrazinyl, hydroxythienyl, methylthienyl, ethylthienyl, methoxythienyl, acetylthienyl, benzoylthienyl, phenylthiothienyl, phenoxythienyl, nitrothienyl, fluorothienyl, chlorothienyl, bromothienyl, hydroxyfuranyl, methylfuranyl, ethylfuranyl, methoxyfuranyl, acetylfuranyl, benzoylfuranyl, phenylthiofuranyl, phenoxyfuranyl, nitrofuranyl, fluorofuranyl, chlorofuranyl, and bromofuranyl are exemplary examples.

As the condensed polycyclic heterocyclic hydrocarbon group, indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthenyl, dibenzofuranyl, hydroxyxanthenyl, methylxanthenyl, ethylxanthenyl, methoxyxanthenyl, acetylxanthenyl, benzoylxanthenyl, phenylthioxanthenyl, phenoxyxanthenyl, nitroxanthenyl, fluoroxanthenyl, chloroxanthenyl, bromoxanthenyl, hydroxythianthrenyl, methylthianthrenyl, ethylthianthrenyl, methoxythianthrenyl, benzoylthianthrenyl, phenylthiothianthrenyl, phenoxythianthrenyl, nitrothianthrenyl, fluorohianthrenyl, chlorothianthrenyl, bromothianthrenyl, hydroxyxanthonyl, methylxanthonyl, dimethylxanthonyl, ethylxanthonyl, diethylxanthonyl, n-propylxanthonyl, isopropylxanthonyl, methoxyxanthonyl, acetylxanthonyl, benzoylxanthonyl, phenylthioxanthonyl, phenoxyxanthonyl, acetoxyxanthonyl, nitroxanthonyl, fluoroxanthonyl, chloroxanthonyl, hydroxythioxanthonyl, methylthioxanthonyl, dimethylthioxanthonyl, ethylthioxanthonyl, diethylthioxanthonyl, n-propylthioxanthonyl, isopropylthioxanthonyl, methoxythioxanthonyl, acetylthioxanthonyl, benzoylthioxanthonyl, phenylthioxanthonyl, phenoxythioxanthonyl, acetoxythioxanthonyl, nitrothioxanthonyl, fluorothioxanthonyl, chlorothioxanthonyl, and bromothioxanthonyl are exemplary examples.

In R1 and R2, as the alkyl group having 1 to 30 carbon atoms, linear alkyl groups (methyl, ethyl, propyl, butyl, pentyl, octyl, decyl, dodecyl, tetradecyl, hexadecyl, octadecyl, benzyl, diphenylmethyl, naphthylmethyl, anthracenylmethyl, phenacyl (—CH$_2$COC$_6$H$_5$), naphthoylmethyl, anthylmethyl, and the like), branched alkyl groups (isopropyl, isobutyl, sec-butyl, tert-butyl, isopentyl, neopentyl, tert-pentyl, isohexyl, and the like), and cycloalkyl groups (cyclopropyl, cyclobutyl, cyclopentyl, cyclohexyl, and the like) are exemplary examples.

It is preferable that R1 and R2 are an aryl group having 6 to 30 carbon atoms, in which a part of hydrogen atoms may be substituted with the substituent (t), or a heterocyclic hydrocarbon group having 4 to 30 carbon atoms, in which a part of hydrogen atoms may be substituted with the substituent (t), it is more preferable that at least one of R1 or R2 is a heterocyclic hydrocarbon group having 4 to 30 carbon atoms, and from the viewpoint of photosensitivity and solubility, it is particularly preferable that R1 is a thioxanthonyl group and R2 is an aryl group having 6 to 30 carbon atoms, which may be substituted with the substituent (t).

As the substituent (t), an alkyl group having 1 to 18 carbon atoms, a hydroxy group, an alkoxy group having 1 to 18 carbon atoms, an alkylcarbonyl group having 2 to 18 carbon atoms, or an arylcarbonyl group having 7 to 11 carbon atoms is preferable, an alkyl group or an alkoxy group is more preferable, and a methyl group, an ethyl group, a propyl group (n-propyl and isopropyl), a butyl group (n-butyl, isobutyl, sec-butyl, and tert-butyl), a methoxy group, or an ethoxy group is particularly preferable.

A cation moiety in the above-described component (I0) is preferably a cation in which A in General Formula (I0) is a group represented by —S— or —O—, and each of k and m is 0 and n is an integer of 1 to 4.

Alternatively, the cation moiety in the above-described component (I0) is preferably a cation in which R1 or R2 in General Formula (I0) is an aryl group having 6 to 30 carbon atoms or a heterocyclic hydrocarbon group having 4 to 30 carbon atoms (in which a part of hydrogen atoms in the aryl group or the heterocyclic hydrocarbon group may be substituted with the substituent (t)).

Alternatively, the cation moiety in the above-described component (I0) is preferably a cation in which R1 or R2 in General Formula (I0) is a thioxanthonyl group in which a part of hydrogen atoms may be substituted with the substituent (t), each of k and m is 0 and n is 1 or 2, and A is a group represented by —S—.

Specifically, as the cation moiety in the above-described component (I0), the following cations are exemplary examples.

(I0-ca-1)

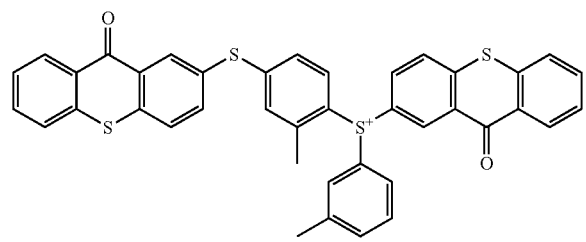

(I0-ca-2)

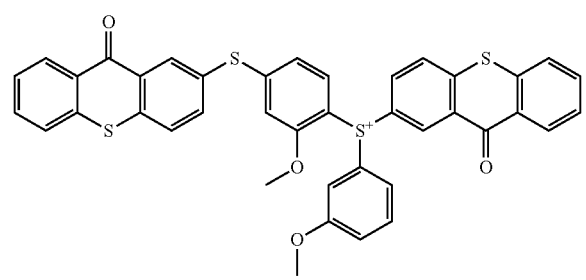

(I0-ca-3)

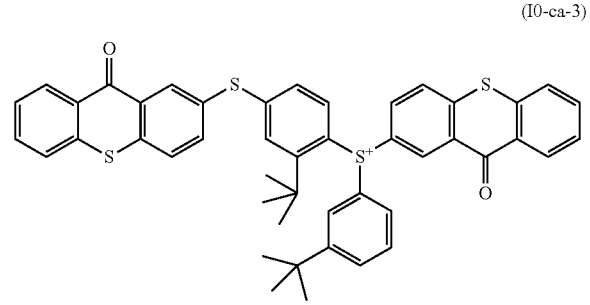

(I0-ca-4)

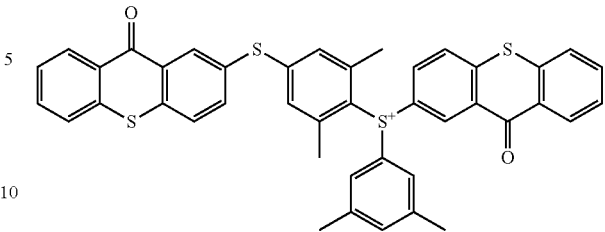

(I0-ca-5)

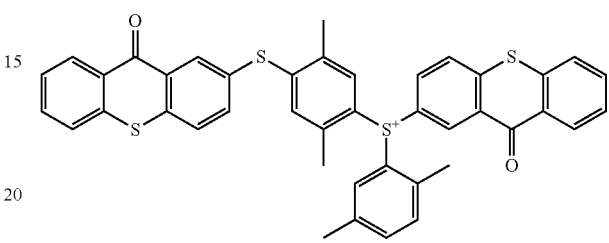

(I0-ca-6)

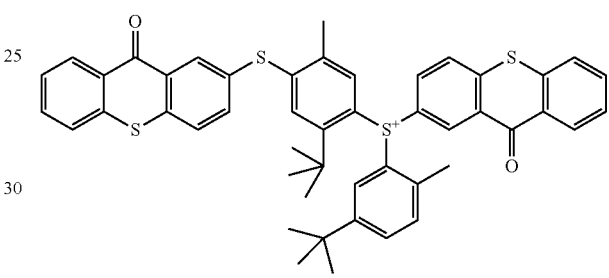

In Formula (I0), $X^-$ is not limited as long as it is a monovalent polyatomic anion, and is an anion corresponding to an acid (HX) generated by irradiating the sulfonium salt (I0) with active energy rays (visible light, ultraviolet rays, electron beams, $X^-$ rays, and the like).

As $X^-$, anions represented by $MY_a^-$, $(Rf)_b PF_{6-b}^-$, $R^6{}_c BY_{4-c}^-$, $R^6{}_c CGaY_{4-c}^-$, $R^7 SO_3^-$, $(R^7 SO_2)_3 C^-$, or $(R^7 SO_2)_2 N^-$ are exemplary examples.

M represents a phosphorus atom, a boron atom, or an antimony atom.

Y represents a halogen atom, and is preferably a fluorine atom.

Rf represents an alkyl group in which 80 mol % or more of hydrogen atoms are substituted with fluorine atoms.

As the alkyl group to be Rf by fluorine substitution, an alkyl group having 1 to 8 carbon atoms is preferable, and linear alkyl groups (methyl, ethyl, propyl, butyl, pentyl, octyl, and the like), branched alkyl groups (isopropyl, isobutyl, sec-butyl, tert-butyl, and the like), and cycloalkyl groups (cyclopropyl, cyclobutyl, cyclopentyl, cyclohexyl, and the like) are exemplary examples.

In Rf, a proportion of hydrogen atoms in these alkyl groups substituted with fluorine atoms is preferably 80 mol % or more, more preferably 90% or more, and particularly preferably 100% based on the number of moles of hydrogen atoms in the original alkyl group. In a case where the substitution proportion with fluorine atoms is within these preferred ranges, the photosensitivity of the sulfonium salt is further improved.

As Rf, $CF_3$—, $CF_3CF_2$—, $(CF_3)_2CF$—, $CF_3CF_2CF_2$—, $CF_3CF_2CF_2CF_2$—, $(CF_3)_2CFCF_2$—, $CF_3CF_2(CF_3)CF$—, and $(CF_3)_3C$— are particularly preferred exemplary examples.

b pieces of Rf's are independent of each other, and may be the same or different from each other.

P represents a phosphorus atom and F represents a fluorine atom.

$R^6$ represents a phenyl group in which a part of hydrogen atoms are substituted with at least one element or electron-withdrawing group. Such one element include a halogen atom, and a fluorine atom, a chlorine atom, and a bromine atom are exemplary examples. As the electron-withdrawing group, a trifluoromethyl group, a nitro group, and a cyano group are exemplary examples. Among these, a phenyl group in which one hydrogen atom is substituted with a fluorine atom or a trifluoromethyl group is preferable.

c pieces of $R^6$'s are independent of each other, and may be the same or different from each other.

B represents a boron atom and Ga represents a gallium atom.

$R^7$ represents an alkyl group having 1 to 20 carbon atoms, a perfluoroalkyl group having 1 to 20 carbon atoms, or an aryl group having 6 to 20 carbon atoms, the alkyl group and the perfluoroalkyl group may be linear, branched, or cyclic, and the alkyl group or the aryl group may be unsubstituted or may have a substituent.

S represents a sulfur atom, O represents an oxygen atom, C represents a carbon atom, and N represents a nitrogen atom.

a represents an integer of 4 to 6.

b is preferably an integer of 1 to 5, more preferably 2 to 4, and particularly preferably 2 or 3.

c is preferably an integer of 1 to 4, and more preferably 4.

As the anion represented by $MY_a^-$, anions represented by $SbF_6^-$, $PF_6^-$, or $BF_4^-$ are exemplary examples.

As the anion represented by $(Rf)_bPF_{6-b}^-$, anions represented by $(CF_3CF_2)_2PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF_4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$, or $(CF_3CF_2CF_2CF_2)_3PF_3^-$ are exemplary examples. Among these, an anion represented by $(CF_3CF_2)_3PF_3^-$, $(CF_3CF_2CF_2)_3PF_3^-$, $((CF_3)_2CF)_3PF_3^-$, $((CF_3)_2CF)_2PF_4^-$, $((CF_3)_2CFCF_2)_3PF_3^-$, or $((CF_3)_2CFCF_2)_2PF_4^-$ is preferable.

As the anion represented by $R^6_cBY_{4-c}^-$, anions represented by $(C_6F_5)_4B^-$, $((CF_3)_2C_6H_3)_4B^-$, $(CF_3C_6H_4)_4B^-$, $(C_6F_5)_2BF_2^-$, $C_6F_5BF_3^-$, or $(C_6H_3F_2)_4B^-$ are exemplary examples. Among these, an anion represented by $(C_6F_5)_4B^-$ or $((CF_3)_2C_6H_3)_4B^-$ is preferable.

As the anion represented by $R^6_cGaY_{4-c}^-$, anions represented by $(C_6F_5)_4Ga^-$, $((CF_3)_2C_6H_3)_4Ga$, $(CF_3C_6H_4)_4Ga$, $(C_6F_5)_2GaF_2^-$, $C_6F_5GaF_3^-$, or $(C_6H_3F_2)_4Ga$ are exemplary examples. Among these, an anion represented by $(C_6F_5)_4Ga$ or $((CF_3)_2C_6H_3)_4Ga$ is preferable.

As the anion represented by $R^7SO_3^-$, a trifluoromethanesulfonate anion, a pentafluoroethanesulfonate anion, a heptafluoropropanesulfonate anion, a nonafluorobutanesulfonate anion, a pentafluorophenylsulfonate anion, a p-toluenesulfonate anion, a benzenesulfonate anion, a camphorsulfonate anion, a methanesulfonate anion, an ethanesulfonate anion, a propanesulfonate anion, and a butanesulfonate anion are exemplary examples. Among these, a trifluoromethanesulfonate anion, a nonafluorobutanesulfonate anion, a methanesulfonate anion, a butanesulfonate anion, a camphorsulfonate anion, a benzenesulfonate anion, or a p-toluenesulfonate anion is preferable.

As the anion represented by $(R^7SO_2)_3C^-$, anions represented by $(CF_3SO_2)_3C^-$, $(C_2F_5SO_2)_3C^-$, $(C_3F_7SO_2)_3C^-$, or $(C_4F_9SO_2)_3C^-$ are exemplary examples.

As the anion represented by $(R^7SO_2)_2N^-$, anions represented by $(CF_3SO_2)_2N^-$, $(C_2F_5SO_2)_2N^-$, $(C_3F_7SO_2)_2N^-$, or $(C_4F_9SO_2)_2N^-$ are exemplary examples.

As the monovalent polyatomic anion, in addition to the anions represented by $MY_a^-$, $(Rf)_bPF_{6-b}^-$, $R^6_cBY_{4-c}^-$, $R^6_cGaY_{4-c}^-$, $R^7SO_3^-$, $(R^7SO_2)_3C^-$, or $(R^7SO_2)_2N^-$, perhalogenate ions ($C_{104}^-$, $BrO4^-$, and the like), halogenated sulfonate ions ($FSO_3^-$, $ClSO_3^-$, and the like), sulfate ions ($CH_3SO_4^-$, $CF_3SO_4^-$, $HSO_4^-$, and the like), carbonate ions ($HCO_3^-$, $CH_3CO_3^-$, and the like), aluminate ions ($AlCl_4^-$, $AlF4^-$, and the like), a hexafluorobismuthate ion ($BiF_6^-$), carboxylate ions ($CH_3COO^-$, $CF_3COO^-$, $C_6HC00^-$, $CH_3C_6H_4COO^-$, $C_6F_5COO^-$, $CF_3C_6H_4COO^-$, and the like), arylboric acid ions ($B(C_6H_5)_4^-$, $CH_3CH_2CH_2CH_2B(C_6H_5)_3^-$, and the like), a thiocyanate ion ($SCN^-$), a nitrate ion ($NO_3^-$), or the like can be used.

Among these X's, an anion represented by $MY_a^-$, $(Rf)_bPF_{6-b}^-$, $R^6_cBY_{4-c}^-$, $R^6_cGaY_{4-c}^-$, $R^7SO_3^-$, $(R^7SO_2)_3C^-$, or $(R^7SO_2)_2N^-$ is preferable.

For example, from the viewpoint of high cationic polymerizability, $SbF_6^-$, $PF_6^-$, $(CF_3CF_2)_3PF_3^-$, $(C_6F_5)_4B^-$, $((CF_3)_2C_6H_3)_4B^-$, $(C_6F_5)_4Ga$, or $((CF_3)_2C_6H_3)_4Ga$ is preferable.

In addition, from the viewpoint of resist resolution and pattern shape improvement, $(CF_3CF_2)_3PF_3^-$, $(C_6F_5)_4B^-$, $((CF_3)_2C_6H_3)_4B^-$, $(C_6F_5)_4Ga^-$, $((CF_3)_2C_6H_3)_4Ga^-$, a trifluoromethanesulfonate anion, a nonafluorobutanesulfonate anion, a methanesulfonate anion, a butanesulfonate anion, a camphorsulfonate anion, a benzenesulfonate anion, p-toluenesulfonate anion, $(CF_3SO_2)_3C^-$, or $(CF_3SO_2)_2N^-$ is preferable.

Furthermore, from the viewpoint of good compatibility of the cationic polymerizable compound with a resist composition, $(CF_3CF_2)_3PF_3^-$, a nonafluorobutanesulfonate anion, $(C_6F_5)_4B^-$, $((CF_3)_2C_6H_3)_4B^-$, or $(CF_3SO_2)_3C^-$ is particularly preferable.

In addition, $(C_6F_5)_4Ga^-$ is still more preferable from the viewpoint of excellent heat-resistant transparency.

In particular, in the negative photosensitive resin composition according to the present embodiment, from the viewpoint that the resolution of the pattern can be improved more easily, the anion moiety of the component (I0) is preferably $(Rf)_bPF_{6-b}^-$ or $R^6_cBY_{4-c}^-$.

Specific examples of the suitable component (I0) are shown below.

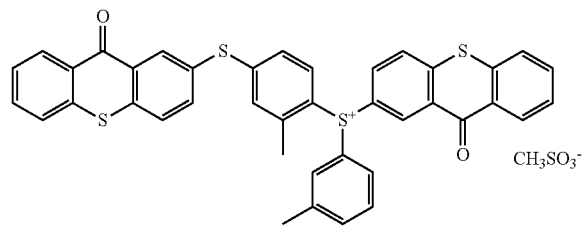

(I0-01)

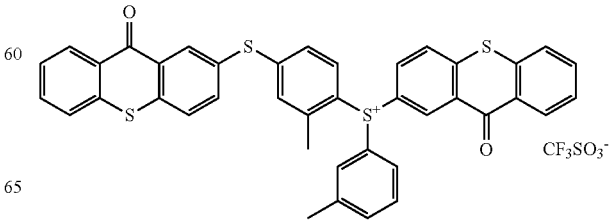

(I0-02)

(I0-03)
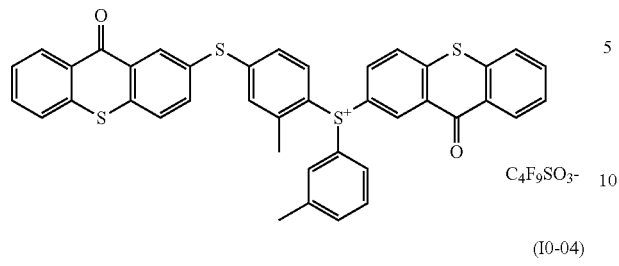
C₄F₉SO₃⁻
(I0-04)
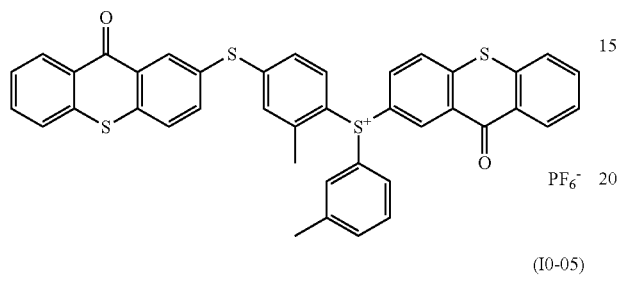
PF₆⁻
(I0-05)
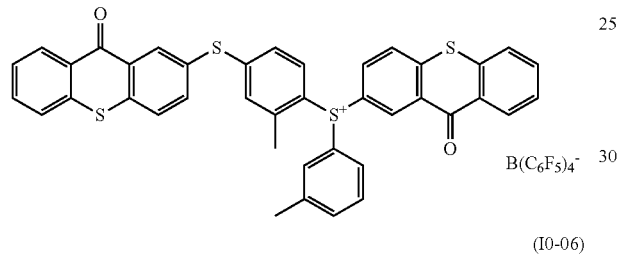
B(C₆F₅)₄⁻
(I0-06)
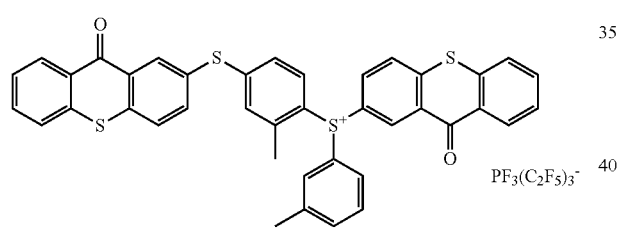
PF₃(C₂F₅)₃⁻
(I0-07)
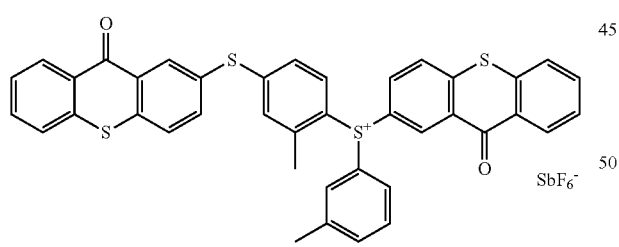
SbF₆⁻
(I0-08)
Ga(C₆F₅)₄⁻
(I0-09)
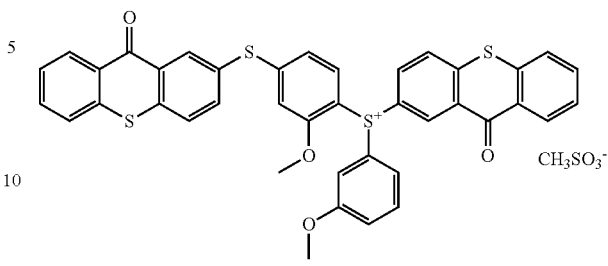
CH₃SO₃⁻
(I0-10)
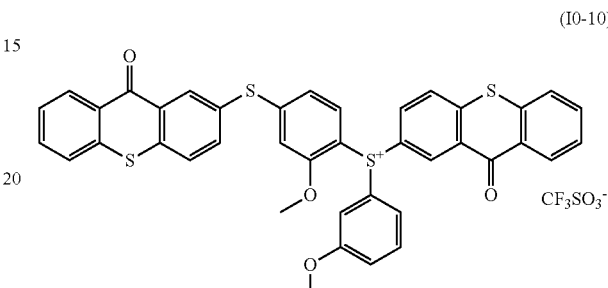
CF₃SO₃⁻
(I0-11)
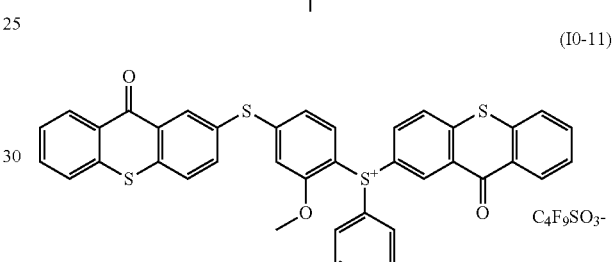
C₄F₉SO₃⁻
(I0-12)
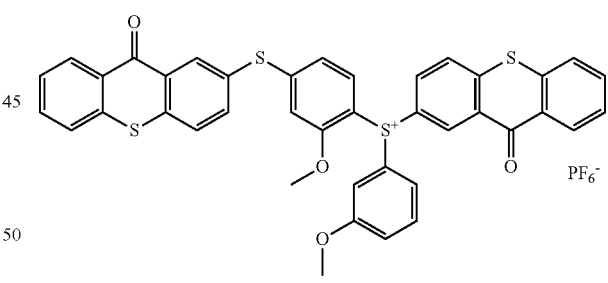
PF₆⁻
(I0-13)
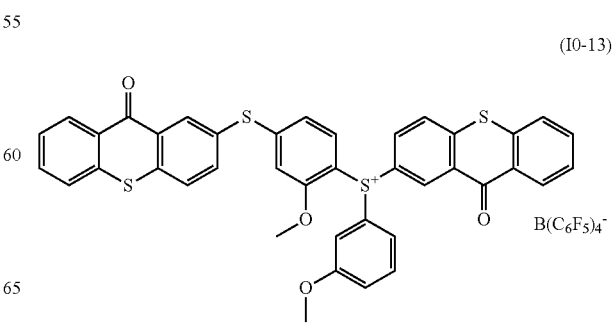
B(C₆F₅)₄⁻

(I0-14)
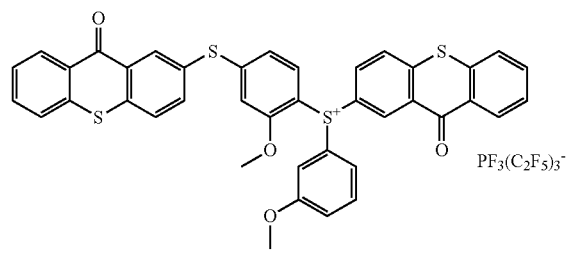
PF$_3$(C$_2$F$_5$)$_3^-$
(I0-15)
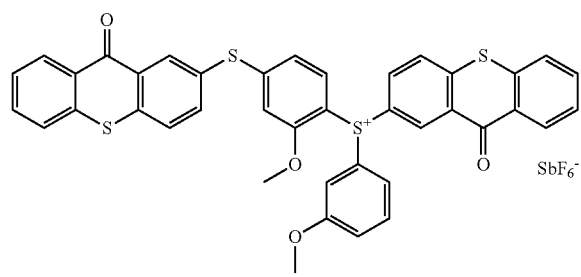
SbF$_6^-$
(I0-16)
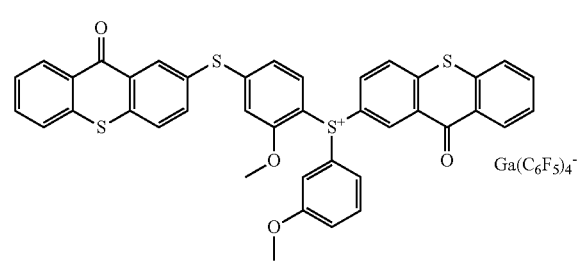
Ga(C$_6$F$_5$)$_4^-$
(I0-17)
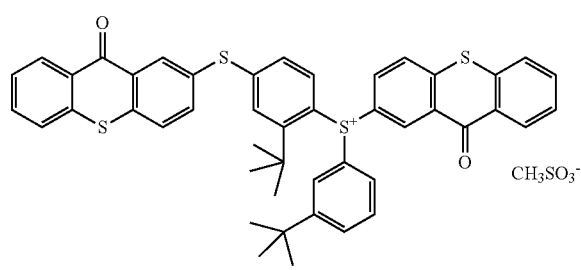
CH$_3$SO$_3^-$
(I0-18)
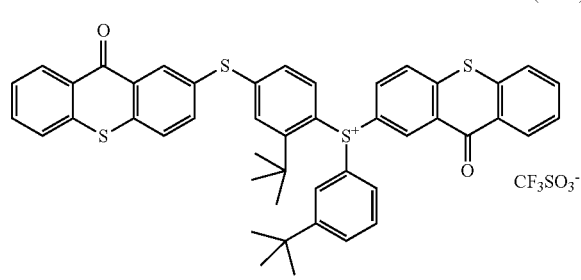
CF$_3$SO$_3^-$
(I0-19)
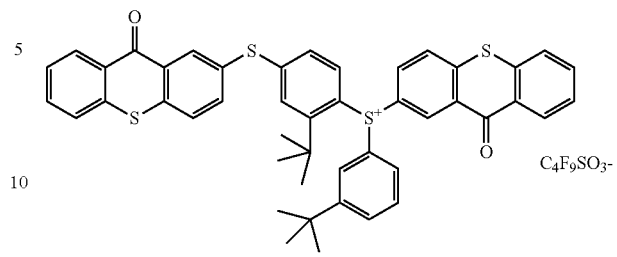
C$_4$F$_9$SO$_3^-$
(I0-20)
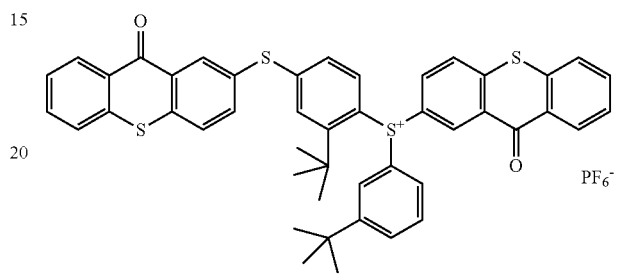
PF$_6^-$
(I0-21)
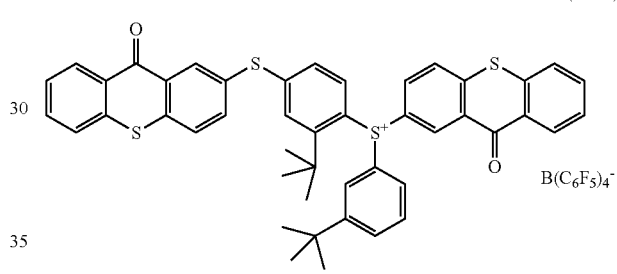
B(C$_6$F$_5$)$_4^-$
(I0-22)
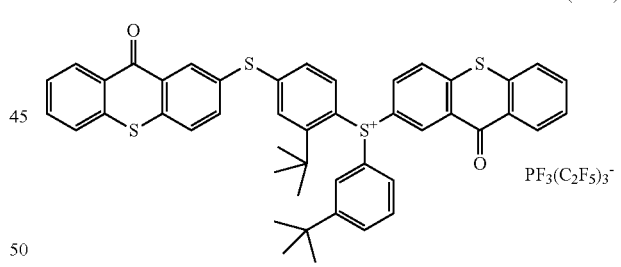
PF$_3$(C$_2$F$_5$)$_3^-$
(I0-23)
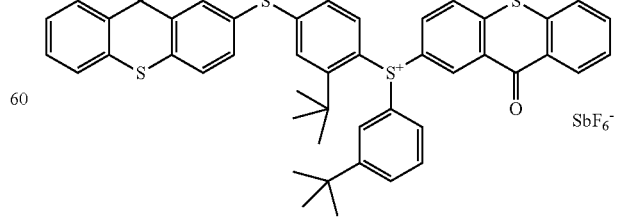
SbF$_6^-$ (I0-24)
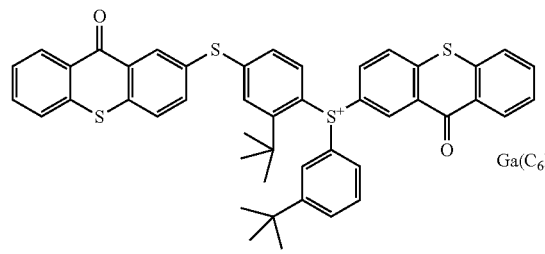
Ga(C₆F₅)₄⁻
(I0-25)
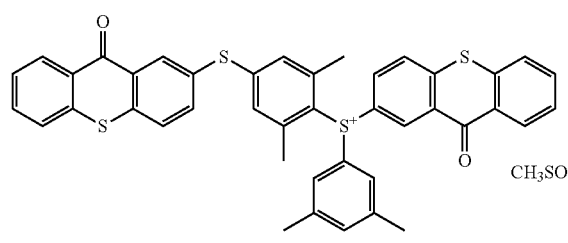
CH₃SO₃⁻
(I0-26)
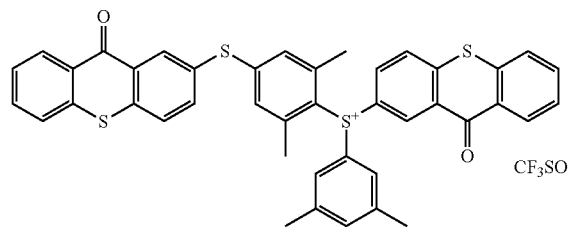
CF₃SO₃⁻
(I0-27)
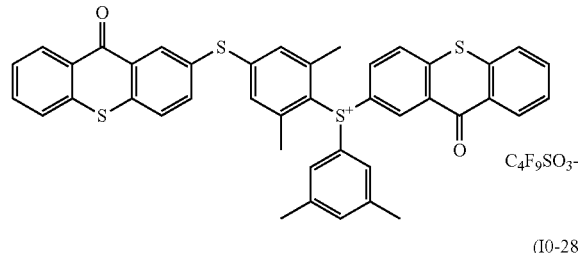
C₄F₉SO₃⁻
(I0-28)
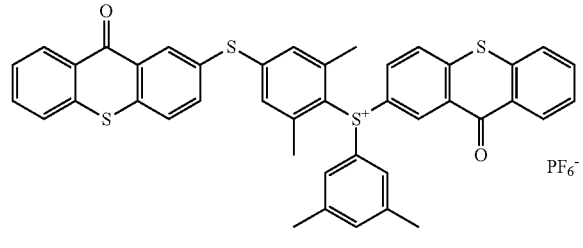
PF₆⁻
(I0-29)
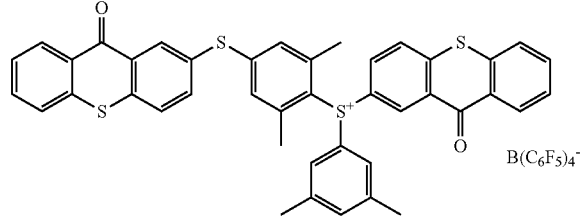
B(C₆F₅)₄⁻
(I0-30)
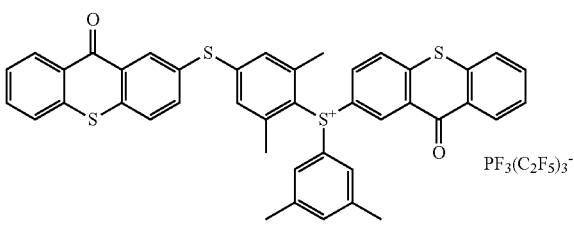
PF₃(C₂F₅)₃⁻
(I0-31)
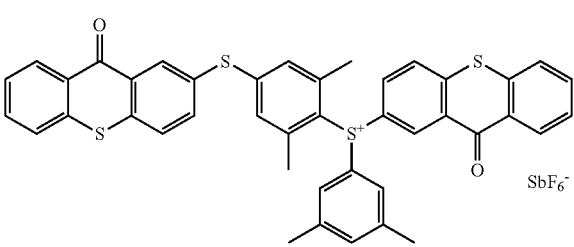
SbF₆⁻
(I0-32)
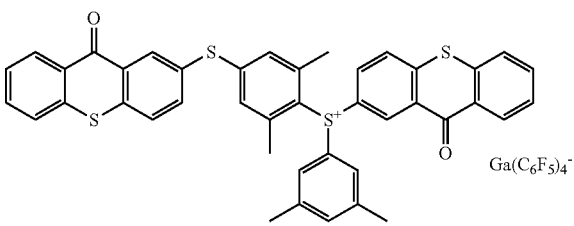
Ga(C₆F₅)₄⁻
(10-33)
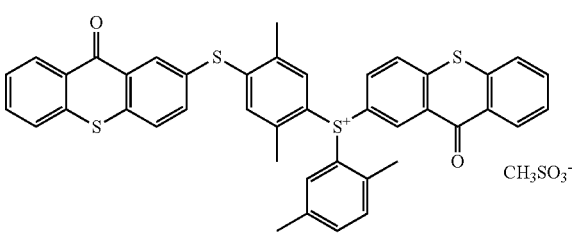
CH₃SO₃⁻
(10-34)
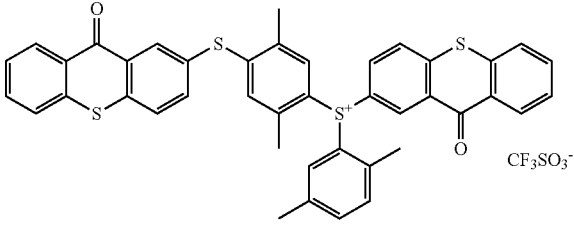
CF₃SO₃⁻
(10-35)
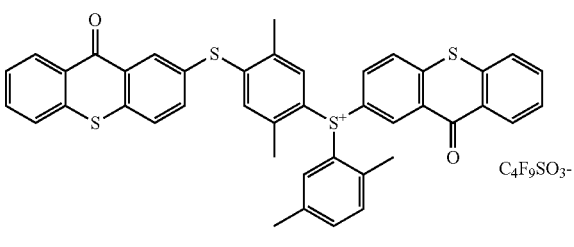
C₄F₉SO₃⁻

-continued
(10-36)
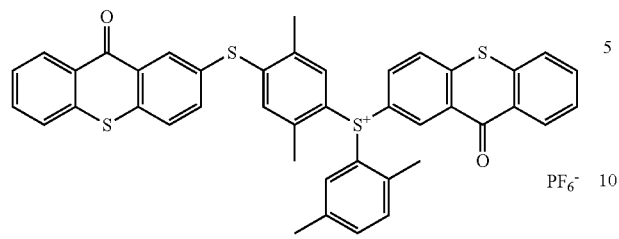
PF$_6^-$
(10-37)
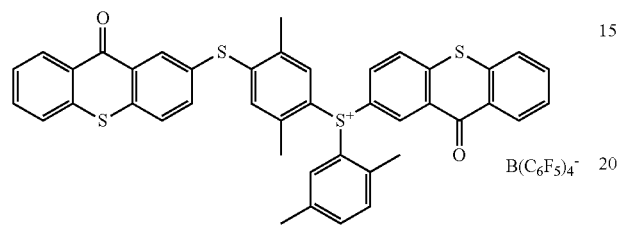
B(C$_6$F$_5$)$_4^-$
(10-38)
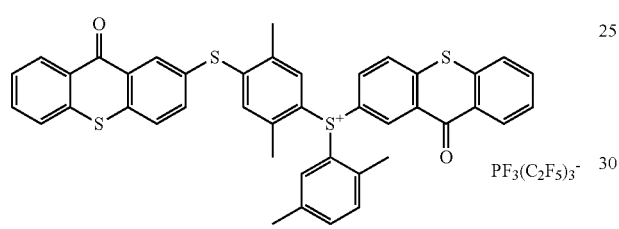
PF$_3$(C$_2$F$_5$)$_3^-$
(10-39)
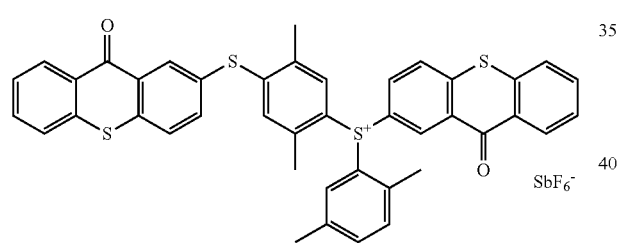
SbF$_6^-$
(10-40)
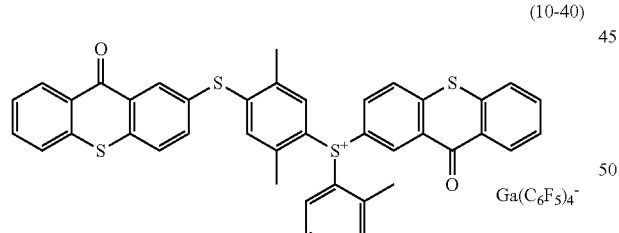
Ga(C$_6$F$_5$)$_4^-$
(I0-41)
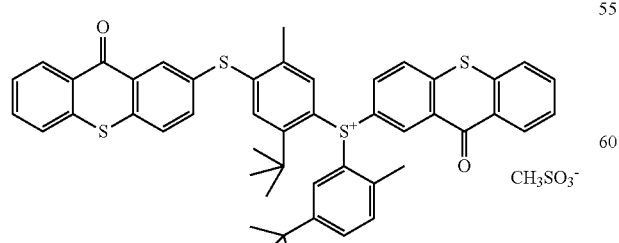
CH$_3$SO$_3^-$
-continued
(I0-42)
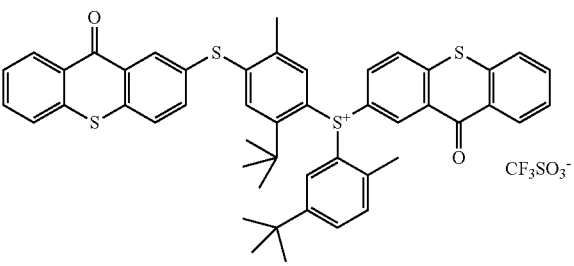
CF$_3$SO$_3^-$
(I0-43)
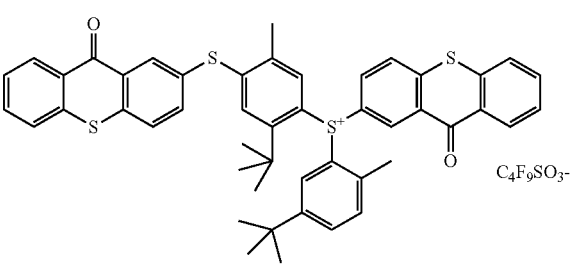
C$_4$F$_9$SO$_3^-$
(I0-44)
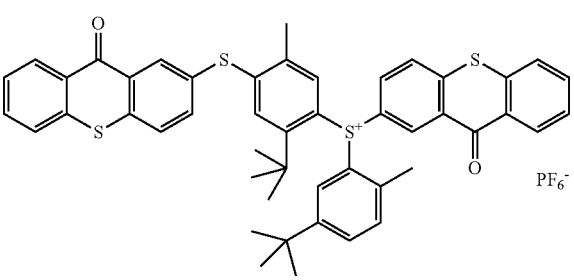
PF$_6^-$
(I0-45)
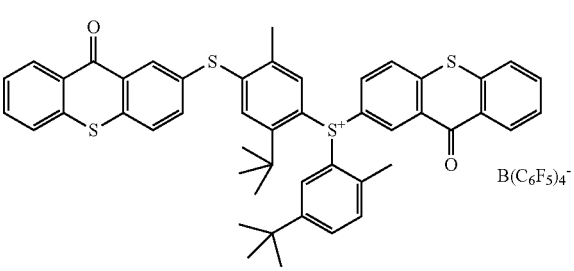
B(C$_6$F$_5$)$_4^-$
(I0-46)
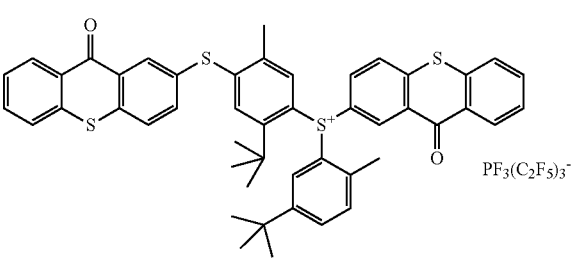
PF$_3$(C$_2$F$_5$)$_3^-$ -continued (I0-47)

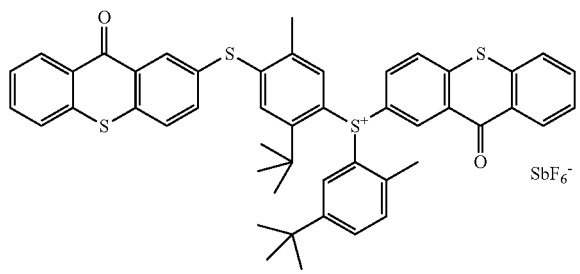

(I0-48)

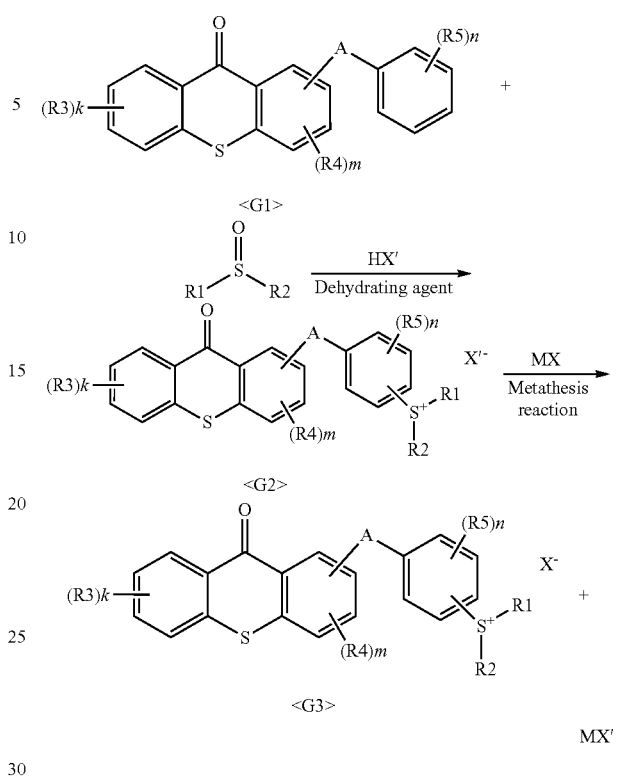

The component (I0) may be used alone or in combination of two or more kinds thereof.

The component (I0) is preferably at least one selected from the group consisting of the compounds (I0-01) to (I0-48) described above, more preferably at least one selected from the group consisting of the compounds (I0-25) to (I0-48), and still more preferably at least one selected from the group consisting of the compounds (10-41) to (I0-48).

In the photosensitive composition according to the present embodiment, a content of the component (I0) is preferably 0.1 to 5 parts by mass, more preferably 0.3 to 4.5 parts by mass, and still more preferably 0.5 to 4 parts by mass with respect to 100 parts by mass of the component (A).

In a case where the content of the component (I0) is more than or equal to the lower limit value of the above-described preferred range, sufficient sensitivity is obtained and resolution of the pattern is further improved. In addition, the hardness of the cured film is further enhanced. On the other hand, in a case of being less than or equal to the upper limit value of the above-described preferred range, the sensitivity is appropriately controlled and a pattern having a favorable shape is easily obtained.

[Sulfonium Salt (I0) Production Method]

The sulfonium salt (I0) in the present embodiment can be produced by a production method described below.

Method represented by the following reaction formula (for example, methods described in Lectures of Experimental Chemistry, 4th Edition, vol. 24, p. 376, published by Maruzen Co., Ltd. (1992), Japanese Unexamined Patent Application, First Publication No. $H_7$-329399, Japanese Unexamined Patent Application, First Publication No. $H_8$-165290, Japanese Unexamined Patent Application, First Publication No. $H_{10}$-212286, or Japanese Unexamined Patent Application, First Publication No. $H_{10}$-7680)

In the above reaction formula, R1 to R5, A, S, O, $X^-$, k, m, and n have the same definitions of R1 to R5, A, S, O, $X^-$, k, m, and n in General Formula (I0) described above. H represents a hydrogen atom.

HX' represents a conjugate acid of the monovalent polyatomic anion. As HX', from the viewpoint of availability, acid stability, and reaction yield, a methanesulfonic acid, a perfluoromethanesulfonic acid, or a sulfuric acid is preferable. The dehydrating agent represents, for example, phosphoric anhydride, acetic anhydride, concentrated sulfuric acid, or the like.

The monovalent polyatomic anion ($X'^-$) can be exchanged for other anions ($X^-$), for example, by a metathesis reaction as described above.

MX represents a salt of a alkali metal (lithium, sodium, potassium, and the like) cation and other anions described above {for example, anions represented by $MY_a^-$, $(Rf)_b PF_{6-b}^-$, $R^6 cBY_{4-c}^-$, $R^6_c GaY_{4-c}^-$, $R^7 SO_3^-$, $(R^7 SO_2)_3 C^-$, $(R^7 SO_2)_2 N^-$, or the like}.

In the above reaction formula, the reaction in the first stage may be carried out with a solvent, or may be carried out in an organic solvent (acetonitrile, tetrahydrofuran, dioxane, ethanol, acetone, or the like) as necessary. The reaction temperature is approximately 20° C. to 105° C.

The reaction in the second stage may be carried out following the reaction in the first stage, or may be carried out after a reaction intermediate (G2) is isolated (and purified as necessary).

The reaction intermediate (G2) and an aqueous solution of the salt (MX) of the alkali metal cation and the other anions are mixed and stirred to perform a metathesis reaction, and the precipitated solid is filtered off or the separated oil is extracted with an organic solvent to remove the organic solvent, thereby obtaining the sulfonium salt (I0) as a solid or a viscous liquid. The obtained solid or viscous liquid can be washed with an appropriate organic solvent as necessary, or purified by recrystallization or column chromatography.

A chemical structure of the sulfonium salt (I0) can be identified by general analytical techniques (for example, $^1$H—, $^{11}$B—, $^{13}$C—, $^{19}$F—, or $^{31}$P-nuclear magnetic resonance spectrum, infrared absorption spectrum, elemental analysis, and/or the like).

<<Cationic Polymerization Initiator Other than Component (I0)>>

In the photosensitive composition according to the present embodiment, as the component (I), in addition to the component (I0), a cationic polymerization initiator other than the component (I0) may be used in combination.

The cationic polymerization initiator other than the component (I0) is not particularly limited, and a cationic polymerization initiator having different cation moiety in the component (I0) described above is an exemplary example.

As the cation different from the cation moiety in the component (I0) described above, a sulfonium cation and an iodonium cation are suitable exemplary examples. In addition, organic cations represented by General Formulae (ca-1) to (ca-5) are particularly preferable.

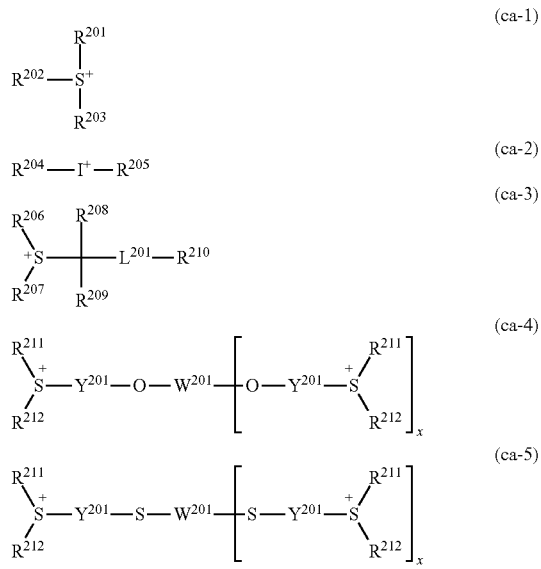

[in the formulae, $R^{201}$ to $R^{207}$, $R^{211}$, and $R^{212}$ each independently represent an aryl group which may have a substituent, a heteroaryl group which may have a substituent, an alkyl group which may have a substituent, or an alkenyl group which may have a substituent, $R^{201}$ to $R^{203}$, $R^{206}$ and $R^{207}$, and $R^{211}$ and $R^{212}$ may be bonded to one another to form a ring together with a sulfur atom in the formulae, $R^{208}$ and $R^{209}$ each independently represent a hydrogen atom or an alkyl group having 1 to 5 carbon atoms, $R^{210}$ represents an aryl group which may have a substituent, an alkyl group which may have a substituent, an alkenyl group which may have a substituent, or a —SO$_2$-containing cyclic group which may have a substituent, $L^{201}$ represents —C(=O)— or —C(=O)—O—, $Y^{201}$'s each independently represent an arylene group, an alkylene group, or an alkenylene group, x represents 1 or 2, and $W^{201}$ represents an (x+1)-valent linking group]

As the aryl group in $R^{201}$ to $R^{207}$, and $R^{211}$ and $R^{212}$, substituted or unsubstituted aryl groups having 6 to 20 carbon atoms are examples. Among these, a phenyl group or a naphthyl group is preferable.

As the heteroaryl group in $R^{201}$ to $R^{207}$, and $R^{211}$ and $R^{212}$, those in which a part of carbon atoms constituting the aryl group are substituted with a hetero atom are exemplary examples.

As the hetero atom, an oxygen atom, a sulfur atom, and a nitrogen atom are exemplary examples. As the heteroaryl group, a group formed by removing one hydrogen atom from 9H-thioxanthene is an exemplary example, and as the substituted heteroaryl group, a group formed by removing one hydrogen atom from 9H-thioxanthene-9-one is an exemplary example.

As the alkyl group in $R^{201}$ to $R^{207}$, and $R^{211}$ and $R^{212}$, a chain-like or cyclic alkyl group having 1 to 30 carbon atoms is preferable.

As the alkenyl group in $R^{201}$ to $R^{207}$, and $R^{211}$ and $R^{212}$, an alkenyl group having 2 to 10 carbon atoms is preferable.

As the substituent which may be included in $R^{201}$ to $R^{207}$, and $R^{210}$ to $R^{212}$, for example, an alkyl group, a halogen atom, a halogenated alkyl group, a carbonyl group, a cyano group, an amino group, an oxo group (=O), an aryl group, and groups represented by Formulae (ca-r-1) to (ca-r-10) are exemplary examples.

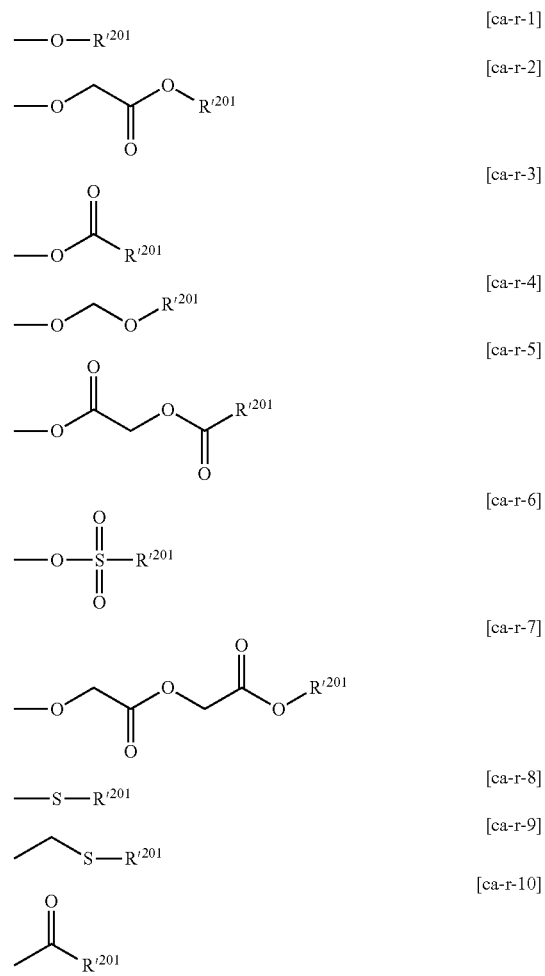

[in the formulae, $R'^{201}$'s are each independently a hydrogen atom, a cyclic group which may have a substituent, a chain-like alkyl group which may have a substituent, or a chain-like alkenyl group which may have a substituent]

In Formulae (ca-r-1) to (ca-r-10), $R'^{201}$'s are each independently a hydrogen atom, a cyclic group which may have a substituent, a chain-like alkyl group which may have a substituent, or a chain-like alkenyl group which may have a substituent.

Cyclic group which may have substituent:

it is preferable that the cyclic group is a cyclic hydrocarbon group, and the cyclic hydrocarbon group may be an aromatic hydrocarbon group or a cyclic aliphatic hydrocarbon group. The aliphatic hydrocarbon group indicates a hydrocarbon group with no aromaticity. Further, the aliphatic hydrocarbon group may be saturated or unsaturated. In general, it is preferable that the aliphatic hydrocarbon group is saturated.

The aromatic hydrocarbon group in $R'^{201}$ is a hydrocarbon group having an aromatic ring. The number of carbon atoms in the aromatic hydrocarbon group is preferably 3 to 30, more preferably 5 to 30, still more preferably 5 to 20, particularly preferably 6 to 15, and most preferably 6 to 10. Here, the number of carbon atoms thereof does not include the number of carbon atoms in a substituent.

Specifically, as the aromatic ring included in the aromatic hydrocarbon group in $R'^{201}$, benzene, fluorene, naphthalene, anthracene, phenanthrene, biphenyl, an aromatic heterocyclic ring in which a part of carbon atoms constituting any of these aromatic rings are substituted with hetero atom, and a ring in which a part of hydrogen atoms constituting any of these aromatic rings or aromatic heterocyclic rings are substituted with an oxo group are exemplary examples. As the hetero atom in the aromatic heterocyclic ring, an oxygen atom, a sulfur atom, and a nitrogen atom are exemplary examples.

Specifically, as the aromatic hydrocarbon group in $R'^{201}$, a group (an aryl group such as a phenyl group, a naphthyl group, or an anthracenyl group) formed by removing one hydrogen atom from the aromatic ring; a group (an arylalkyl group such as a benzyl group, a phenethyl group, a 1-naphthylmethyl group, a 2-naphthylmethyl group, a 1-naphthylethyl group, and a 2-naphthylethyl group, and the like) in which one hydrogen atom in the aromatic ring is substituted with an alkylene group; a group formed by removing one hydrogen atom from a ring (such as anthraquinone) in which a part of hydrogen atoms constituting the aromatic ring is substituted with an oxo group and the like; and a group formed by removing one hydrogen atom from an aromatic heterocyclic ring (such as 9H-thioxanthene or 9H-thioxanthen-9-one) are exemplary examples. The number of carbon atoms in the above-described alkylene group (an alkyl chain in the arylalkyl group) is preferably 1 to 4, more preferably 1 or 2, and particularly preferably 1.

As the cyclic aliphatic hydrocarbon group in $R'^{201}$, aliphatic hydrocarbon groups including a ring in the structure thereof are exemplary examples.

As the aliphatic hydrocarbon group including a ring in the structure thereof, an alicyclic hydrocarbon group (a group formed by removing one hydrogen atom from an aliphatic hydrocarbon ring), a group in which an alicyclic hydrocarbon group is bonded to the terminal of a linear or branched aliphatic hydrocarbon group, and a group in which an alicyclic hydrocarbon group is interposed in a linear or branched aliphatic hydrocarbon group are exemplary examples.

The number of carbon atoms in the alicyclic hydrocarbon group is preferably 3 to 20 and more preferably 3 to 12.

The alicyclic hydrocarbon group may be a polycyclic group or a monocyclic group. As the monocyclic alicyclic hydrocarbon group, a group formed by removing one or more hydrogen atoms from a monocycloalkane is preferable. The number of carbon atoms in the monocycloalkane is preferably 3 to 6, and specifically, cyclopentane and cyclohexane are exemplary examples. As the polycyclic alicyclic hydrocarbon group, a group formed by removing one or more hydrogen atoms from a polycycloalkane is preferable, and the number of carbon atoms in the polycycloalkane is preferably 7 to 30. Among these, a polycycloalkane having a bridged ring polycyclic skeleton, such as adamantane, norbornane, isobornane, tricyclodecane, or tetracyclododecane, and a polycycloalkane having a fused ring polycyclic skeleton, such as a cyclic group having a steroid skeleton are more preferable.

Among these examples, as the cyclic aliphatic hydrocarbon group in $R'^{201}$, a group formed by removing one or more hydrogen atoms from a monocycloalkane or a polycycloalkane is preferable, a group formed by removing one hydrogen atom from a polycycloalkane is more preferable, an adamantyl group or a norbornyl group is particularly preferable, and an adamantyl group is most preferable.

The number of carbon atoms in the linear or branched aliphatic hydrocarbon group which may be bonded to the alicyclic hydrocarbon group is preferably 1 to 10, more preferably 1 to 6, still more preferably 1 to 4, and most preferably 1 to 3. As the linear aliphatic hydrocarbon group, a linear alkylene group is preferable. Specifically, a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—] are exemplary examples.

As the branched aliphatic hydrocarbon group, a branched alkylene group is preferable. Specifically, alkylalkylene groups, for example, alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2$CH($CH_3$)$CH_2$—; and alkyltetramethylene groups such as —CH($CH_3$)$CH_2CH_2CH_2$— and —$CH_2$CH($CH_3$)$CH_2CH_2$— are exemplary examples. As an alkyl group in the alkylalkylene group, a linear alkyl group having 1 to 5 carbon atoms is preferable.

Chain-like alkyl group which may have substituent:

the chain-like alkyl group as $R'^{201}$ may be linear or branched.

The number of carbon atoms in the linear alkyl group is preferably 1 to 20, more preferably 1 to 15, and most preferably 1 to 10. Specifically, a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group, and a docosyl group are exemplary examples.

The number of carbon atoms in the branched alkyl group is preferably 3 to 20, more preferably 3 to 15, and most preferably 3 to 10. Specifically, a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group are exemplary examples.

Chain-like alkenyl group which may have substituent:

the chain-like alkenyl group as $R'^{201}$ may be linear or branched, and the number of carbon atoms in the chain-like alkenyl group is preferably 2 to 10, more preferably 2 to 5, still more preferably 2 to 4, and particularly preferably 3. As the linear alkenyl group, a vinyl group, a propenyl group (an allyl group), and a butynyl group are exemplary examples. As the branched alkenyl group, a 1-methylvinyl group, a 2-methylvinyl group, a 1-methylpropenyl group, and a 2-methylpropenyl group are exemplary examples.

Among these examples, as the chain-like alkenyl group, a linear alkenyl group is preferable, a vinyl group or a propenyl group is more preferable, and a vinyl group is particularly preferable.

As the substituent in the cyclic group, the chain-like alkyl group, or the chain-like alkenyl group as $R'^{201}$, an alkoxy group, a halogen atom, a halogenated alkyl group, a hydroxyl group, a carbonyl group, a nitro group, an amino group, an oxo group, the cyclic group in $R'^{201}$, an alkylcarbonyl group, and a thienylcarbonyl group are exemplary examples.

Among these, it is preferable that $R'^{201}$ is a cyclic group which may have a substituent or a chain-like alkyl group which may have a substituent.

In a case where $R^{201}$ to $R^{203}$, $R^{206}$ and $R^{207}$, and $R^{211}$ and $R^{212}$ are bonded to one another to form a ring together with the sulfur atom in the formula, these groups may be bonded to one another through a hetero atom such as a sulfur atom, an oxygen atom, or a nitrogen atom, or a functional group such as a carbonyl group, —SO—, —SO$_2$—, —SO$_3^-$, —COO$^-$, —CONH—, or —N(RN)— (here, RN is an alkyl group having 1 to 5 carbon atoms). As a ring to be formed, one ring containing the sulfur atom in the formula in the ring skeleton thereof is preferably a 3- to 10-membered ring and particularly preferably a 5- to 7-membered ring, including the sulfur atom. Specifically, as the ring to be formed, a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring are exemplary examples.

In Formula (ca-3), $R^{208}$ and $R^{209}$ each independently represent a hydrogen atom or an alkyl group having 1 to 5 carbon atoms and preferably a hydrogen atom or an alkyl group having 1 to 3 carbon atoms. In a case where $R^{208}$ and $R^{209}$ each represent an alkyl group, $R^{208}$ and $R^{209}$ may be bonded to each other to form a ring.

In Formula (ca-3), $R^{210}$ represents an aryl group which may have a substituent, an alkyl group which may have a substituent, an alkenyl group which may have a substituent, or a —SO$_2$-containing cyclic group which may have a substituent.

AS the aryl group in $R^{210}$, unsubstituted aryl groups having 6 to 20 carbon atoms are exemplary examples, and a phenyl group or a naphthyl group is preferable.

As the alkyl group in $R^{210}$, a chain-like or cyclic alkyl group having 1 to 30 carbon atoms is preferable.

The number of carbon atoms in the alkenyl group in $R^{210}$ is preferably 2 to 10.

In Formulae (ca-4) and (ca-5), $Y^{201}$'s each independently represent an arylene group, an alkylene group, or an alkenylene group.

As the arylene group in $Y^{201}$, groups formed by removing one hydrogen atom from an aryl group of exemplary examples as the aromatic hydrocarbon group in $R'^{201}$ are exemplary examples.

As the alkylene group and alkenylene group in $Y^{201}$, groups formed by removing one hydrogen atom from a group of exemplary examples as the chain-like alkyl group or the chain-like alkenyl group in $R'^{201}$ are exemplary examples.

In Formulae (ca-4) and (ca-5), x is 1 or 2.

$W^{201}$ is an (x+1)-valent linking group, that is, a divalent or trivalent linking group.

As the divalent linking group in $W^{201}$, a divalent hydrocarbon group which may have a substituent is preferable. Further, the same divalent hydrocarbon groups which may have a substituent as exemplary examples in the section of $R^{EP}$ in Formula (A1) are preferable. The divalent linking group in $W^{201}$ may be linear, branched, or cyclic, and a cyclic divalent linking group is preferable. Among these, a group formed by combining two carbonyl groups at both ends of an arylene group or a group formed of only an arylene group is preferable. As the arylene group, a phenylene group and a naphthylene group are exemplary examples. Among these, a phenylene group is particularly preferable.

As the trivalent linking group in $W^{201}$, a group formed by removing one hydrogen atom from the divalent linking group in $W^{201}$ and a group in which the divalent linking group is bonded to the divalent linking group are exemplary examples. As the trivalent linking group in $W^{201}$, a group in which two carbonyl groups are bonded to an arylene group is preferable.

As an anion moiety in the cationic polymerization initiator other than the component (I0), a sulfonate anion is preferable. As the sulfonate anion, the above-described anion represented by $R^7SO_3$ is an exemplary example, and a camphorsulfonate anion is particularly preferable.

In the photosensitive composition according to the present embodiment, a content of the cationic polymerization initiator other than the component (I0) in a case of being used in combination is preferably 0.1 to 10 parts by mass, more preferably 0.3 to 5 parts by mass, and still more preferably 0.5 to 2 parts by mass with respect to 100 parts by mass of the component (A).

<Other Components>

The photosensitive resin composition according to the present embodiment may contain other components as necessary, in addition to the component (A) and component (I) described above.

In the photosensitive resin composition according to the embodiment, it is possible to optionally add and contain miscible additives such as a metal oxide (M), a silane coupling agent, a sensitizer component, a solvent, an additive resin for improving film performance, a dissolution inhibitor, a basic compound, a plasticizer, a stabilizer, a colorant, and a halation-preventing agent.

<<Metal Oxide (M)>>

In addition to the component (A) and the component (I), the photosensitive resin composition according to the present embodiment may contain a metal oxide (M) (hereinafter, also referred to as a "component (M)") since a cured film with increased hardness is easily obtained. In addition, by including the component (M), a high-resolution pattern can be formed with a favorable shape.

As the component (M), oxides of metals such as silicon (metallic silicon), titanium, zirconium, and hafnium are exemplary examples. Among these, an oxide of silicon is preferable. In addition, it is particularly preferable to use silica.

In addition, it is preferable that the component (M) is particulate.

Such a particulate component (M) is formed of preferably a group consisting of particles having a volume average particle diameter of 5 to 40 nm, more preferably a group consisting of particles having a volume average particle diameter of 5 to 30 nm, and still more preferably a group consisting of particles having a volume average particle diameter of 10 to 20 nm.

In a case where the volume average particle diameter of the component (M) is greater than or equal to the lower limit value of the above-described preferred range, the hardness of the cured film is likely to be increased. On the other hand, in a case of being less than or equal to the upper limit value of the above-described preferred range, residues are unlikely to be generated during pattern formation, and a pattern with higher resolution is easily formed. In addition, the transparency of the resin film is enhanced.

A particle diameter of the component (M) may be appropriately selected according to the exposure light source. Typically, it is considered that particles having a particle diameter of 1/10 or less with respect to the wavelength of light are almost not affected by light scattering. Therefore, for example, in a case where a fine structure is formed by photolithography with i-line (365 nm), it is preferable that a group (particularly preferably a group of silica particles) consisting of particles having a primary particle diameter (volume average value) of 10 to 20 nm is used as the component (M).

The component (M) may be used alone or in combination of two or more kinds thereof.

A content of the component (M) in a case of being included is preferably 5 to 50 parts by mass and more preferably 10 to 40 parts by mass with respect to 100 parts by mass of the component (A).

In a case where the content of the component (M) is more than or equal to the lower limit value of the above-described preferred range, the hardness of the cured film is further increased. On the other hand, in a case of being less than or equal to the upper limit value of the above-described preferred range, the transparency of the resin film is further enhanced.

<<Silane Coupling Agent>>

The photosensitive resin composition according to the present embodiment may further contain an adhesive aid in order to improve adhesiveness to the substrate. As the adhesive aid, a silane coupling agent is preferable.

As the silane coupling agent, silane coupling agents having reactive substituents such as a carboxy group, a methacryloyl group, an isocyanate group, and an epoxy group are exemplary examples. Specifically, trimethoxysilylbenzoic acid, γ-methacryloxypropyltrimethoxysilane, vinyltriacetoxysilane, vinyltrimethoxysilane, γ-glycidoxypropyltrimethoxysilane, and β-(3,4-epoxycyclohexyl)ethyltrimethoxysilane are exemplary examples.

The silane coupling agent may be used alone or in combination of two or more kinds thereof.

A content of the silane coupling agent in a case of being included is preferably 2.5 to 20 parts by mass, more preferably 3 to 15 parts by mass, and still more preferably 3 to 10 parts by mass with respect to 100 parts by mass of the component (A).

In a case where the content of the silane coupling agent is within the above-described preferred range, the hardness of the cured film is further increased. In addition, the adhesiveness between the cured film and the substrate is further strengthened.

<<Sensitizer Component>>

The photosensitive resin composition according to the present embodiment may further contain a sensitizer component.

The sensitizer component is not particularly limited as long as it can absorb energy from exposure and transfer the energy to other substances.

Specifically, as the sensitizer component, benzophenone-based photosensitizers such as benzophenone and p,p'-tetramethyldiaminobenzophenone, carbazole-based photosensitizers, acetophenone-based photosensitizers, naphthalene-based photosensitizers such as 1,5-dihydroxynaphthalene, phenol-based photosensitizers, anthracene-based photosensitizers such as 9-ethoxyanthracene, and known photosensitizers such as diacetyl, eosin, rose bengal, pyrene, phenothiazine, and anthrone can be used.

The sensitizer component may be used alone or in combination of two or more kinds thereof.

A content of the sensitizer component in a case of being included is preferably 0.1 to 15 parts by mass, more preferably 0.3 to 10 parts by mass, and still more preferably 0.5 to 5 parts by mass with respect to 100 parts by mass of the component (A).

In a case where the content of the sensitizer component is within the above-described preferred range, the sensitivity and the resolution are further enhanced.

<<Solvent>>

The photosensitive resin composition according to the present embodiment may further contain a solvent (hereinafter, may be referred to as a "component (S)").

As the component (S), for example, lactones such as γ-butyrolactone; ketones such as acetone, methyl ethyl ketone (MEK), cyclohexanone, methyl-n-pentyl ketone, methyl isopentyl ketone, and 2-heptanone; polyhydric alcohols such as ethylene glycol, diethylene glycol, propylene glycol, and dipropylene glycol; compounds having an ester bond, such as 2-methoxybutyl acetate, 3-methoxybutyl acetate, 4-methoxybutyl acetate, ethylene glycol monoacetate, diethylene glycol monoacetate, propylene glycol monoacetate, or dipropylene glycol monoacetate; polyhydric alcohol derivatives such as compounds having an ether bond, for example, a monoalkylether such as monomethylether, monoethylether, monopropylether, or monobutylether or monophenylether of any of the polyhydric alcohols or the compounds having an ester bond [among these, propylene glycol monomethyl ether acetate (PGMEA), or propylene glycol monomethyl ether (PGME) is preferable]; cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene, and mesitylene; and dimethylsulfoxide (DMSO) are exemplary examples.

The component (S) may be used alone or in the form of a mixed solvent of two or more kinds thereof.

The amount of the component (S) used in a case of being included is not particularly limited, and is appropriately set according to the thickness of the coating film at a concentration at which the photosensitive composition can be applied to a substrate or the like without dripping.

For example, the component (S) can be used so that the concentration of solid contents is 50% by mass or more, or the component (S) can be used so that the concentration of solid contents is 60% by mass or more.

In addition, an aspect in which the component (S) does not substantially contained (that is, an aspect in which the concentration of solid contents is 100% by mass) can be adopted.

In the negative photosensitive resin composition according to the present embodiment described above, since the negative photosensitive resin composition includes the sulfonium salt (I0) represented by General Formula (I0), compatibility with the epoxy group-containing resin (A) is enhanced, and sensitivity to g-line and h-line is enhanced (pattern can be formed with a lower exposure amount than a method in the related art). As a result, the resolution during the formation of the pattern is further enhanced.

According to the negative photosensitive resin composition of the embodiment, in the formation of the hollow sealing structure, a film having a thickness required for the spacer can be formed, and high-resolution patterning can be performed with a favorable shape and no residue.

In addition, in the negative photosensitive resin composition according to the present embodiment, even in a case where a thick film is formed, the above-described patterning can be similarly performed, and good characteristics are obtained. As a result, the negative photosensitive resin composition according to the present embodiment is also useful as a photosensitive dry film resist.

(Laminated Film)

A laminated film according to the present embodiment is obtained by laminating a photosensitive resin composition layer composed of the negative photosensitive resin composition according to the embodiment described above and a support film.

In the laminated film, a cover film may be disposed on an opposite side of the photosensitive resin composition layer formed of the negative photosensitive resin composition from a side on which the support film is provided.

For example, the laminated film according to the present embodiment can be produced by applying the negative photosensitive resin composition according to the embodiment described above to the support film, drying the negative photosensitive resin composition to form the photosensitive resin composition layer, and laminating the cover film on the photosensitive resin composition layer.

The base film may be coated with the negative photosensitive resin composition according to an appropriate method using a blade coater, a lip coater, a comma coater, a film coater, or the like.

A thickness of the photosensitive resin composition layer is preferably 100 μm or less and more preferably 5 to 50 μm.

A known film can be used as the support film, and for example, a thermoplastic resin film or the like is used. As the thermoplastic resin, polyesters such as polyethylene terephthalate are exemplary examples. A thickness of the base film is preferably 2 to 150 μm.

As the cover film, known films such as a polyethylene film and a polypropylene film are used. As the cover film, a film having an adhesive force to the photosensitive resin composition layer, which is lower than that of the support film, is preferable. A thickness of the cover film is preferably 2 to 150 μm, more preferably 2 to 100 μm, and still more preferably 5 to 50 μm.

The support film and the cover film may be formed of the same film material, or may be formed of different film materials.

(Pattern Formation Method) A pattern formation method according to the present embodiment includes a step of forming a photosensitive resin film on a support (hereinafter, referred to as a "film formation step") using the negative photosensitive resin composition according to the embodiment described above; a step of exposing the photosensitive resin film (hereinafter, referred to as an "exposure step"); and a step of developing the exposed photosensitive resin film with a developing solution containing an organic solvent to form a negative pattern (hereinafter, referred to as a "development step").

For example, the pattern formation method according to the present embodiment can be performed in the following manner.

[Film Formation Step]

First, a photosensitive resin film is formed by coating a support with the negative photosensitive resin composition according to the embodiment using known methods such as a spin coating method, a roll coating method, or a screen printing method and by performing a bake (post apply bake (PAB)) treatment under a temperature condition of, for example, 50° C. to 150° C. for 2 to 60 minutes.

The film forming step can also be performed by disposing the photosensitive resin composition layer of the above-described laminated film on the support.

The support is not particularly limited and a known support in the related art can be used. For example, substrates for electronic parts and substrates on which a predetermined wiring pattern is formed are exemplary examples. More specifically, substrates of metals such as silicon, silicon nitride, titanium, tantalum, lithium tantalate (LiTaO$_3$), niobium, lithium niobate (LiNbO$_3$), palladium, titanium tungsten, copper, chromium, iron, and aluminum, and glass substrates are exemplary examples. As the materials for the wiring pattern, for example, copper, aluminum, nickel, and gold can be used.

In particular, the pattern formation method according to the present embodiment is a method useful for lithium tantalate (LiTaO$_3$) substrates and lithium niobate (LiNbO$_3$) substrates for SAW devices mounted in communication terminals.

A film thickness of the photosensitive resin film to be formed of negative photosensitive resin composition is not particularly limited, but is preferably approximately 10 to 100 μm. Even in a case where a thick film is formed using the negative photosensitive resin composition according to the embodiment described above, favorable characteristics are obtained.

[Exposure Step]

Next, the formed photosensitive resin film is exposed through a mask having a predetermined pattern (mask pattern) formed thereon using a known exposure device or selectively exposed through drawing or the like by performing direct irradiation with electron beams without using a mask pattern therebetween. In addition, a bake (post exposure bake (PEB)) treatment is performed as necessary under a temperature condition of, for example, 80° C. to 150° C. for 40 to 1200 seconds, preferably 40 to 1000 seconds and more preferably 60 to 900 seconds.

The wavelength used in the exposure is not particularly limited, and the exposure is performed by selectively radiating (exposing) radiation, for example, ultraviolet rays having a wavelength of 300 to 500 nm, i-line (wavelength of 365 nm), or visible light rays. As these radiation sources, a low pressure mercury lamp, a high pressure mercury lamp, an ultra-high pressure mercury lamp, a metal halide lamp, and an argon gas laser can be used.

Here, the radiation indicates ultraviolet rays, visible light rays, far ultraviolet rays, X rays, electron beams, or the like. The radiation amount varies depending on the type of each component in the composition, the blending amount thereof, the film thickness of the coating film, and the like. For example, in a case where an ultra-high pressure mercury lamp is used, the radiation amount thereof is 100 to 2000 mJ/cm$^2$.

The photosensitive resin film may be exposed through typical exposure (dry exposure) performed in air or an inert gas such as nitrogen or through liquid immersion exposure (liquid immersion lithography).

The photosensitive resin film after the exposure step is highly transparent, and a haze value in a case of irradiation with i-line (wavelength of 365 nm) is preferably 3% or less and more preferably 1.0% to 2.7%.

As described above, the photosensitive resin film formed of the negative photosensitive resin composition according to the embodiment described above is highly transparent. Therefore, the light transmittance is increased during the exposure in pattern formation so that a negative pattern with favorable lithography characteristics is likely to be obtained.

The haze value of the photosensitive resin film after the exposure step is measured using a method in conformity with JIS K 7136 (2000).

[Development Step]

Next, the above-described exposed photosensitive resin film is developed with a developing solution (organic developing solution) containing an organic solvent. After the development, it is preferable that a rinse treatment is performed. As necessary, a bake treatment (post bake) may be performed.

As the organic solvent contained in the organic developing solution, a solvent which is capable of dissolving the component (A) (component (A) before the exposure) may be used and can be appropriately selected from known organic solvents. Specifically, polar solvents such as ketone solvents, ester solvents, alcohol solvents, nitrile solvents, amide solvents, and ether solvents; and hydrocarbon solvents are exemplary examples.

As the ketone solvents, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetylcarbinol, acetophenone, methyl naphthyl ketone, isophorone, propylenecarbonate, γ-butyrolactone, and methyl amyl ketone (2-heptanone) are exemplary examples. Among these examples, as the ketone solvents, methyl amyl ketone (2-heptanone) is preferable.

As the ester solvents, methyl acetate, butyl acetate, ethyl acetate, isopropyl acetate, amyl acetate, isoamyl acetate, ethyl methoxyacetate, ethyl ethoxyacetate, propylene glycol monomethyl ether acetate (PGMEA), ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate are exemplary examples. Among these examples, as the ester solvents, butyl acetate or PGMEA is preferable.

As the nitrile solvents, acetonitrile, propionitrile, valeronitrile, and butyronitrile are exemplary examples.

Known additives can be blended with the organic developing solution as necessary. As the additive, for example, a surfactant is an exemplary example. The surfactant is not particularly limited, and for example, an ionic or non-ionic fluorine-based and/or silicon-based surfactant can be used.

As the surfactant, a non-ionic surfactant is preferable, and a non-ionic fluorine-based surfactant or a non-ionic silicon-based surfactant is more preferable. In a case where a surfactant is blended, the blending amount thereof is typically 0.001% to 5% by mass, preferably 0.005% to 2% by mass, and more preferably 0.01% to 0.5% by mass with respect to the total amount of the organic developing solution.

The development treatment can be performed by a known developing method. For example, a method of immersing a support in a developing solution for a predetermined time (a dip method), a method of stacking up a developing solution on the surface of a support using the surface tension and maintaining the state for a predetermined time (a puddle method), a method of spraying a developing solution to the surface of a support (a spray method), and a method of continuously ejecting a developing solution from a developing solution ejecting nozzle onto a support rotating at a constant speed while scanning the developing solution ejecting nozzle at a constant speed (a dynamic dispense method) are exemplary examples.

The rinse treatment (washing treatment) using a rinse liquid can be performed according to a known rinse method. As the rinse treatment method, for example, a method of continuously ejecting a rinse liquid onto a support rotating at a constant speed (a rotary coating method), a method of immersing a support in a rinse liquid for a predetermined time (a dip method), and a method of spraying a rinse liquid to the surface of a support (a spray method) are exemplary examples.

In the rinse treatment, it is preferable to use a rinse liquid containing an organic solvent.

By performing the above-described film formation step, exposure step, and development step, a pattern can be formed.

In the pattern formation method according to the embodiment described above, since the above-described negative photosensitive resin composition according to the first aspect is used, a pattern with higher resolution can be formed. In addition, according to the pattern formation method of the embodiment, it is possible to increase the sensitivity, reduce the residue, and form a pattern with a favorable shape.

(Cured Film)

The cured film according to the present embodiment is obtained by curing the above-described negative photosensitive resin composition according to the embodiment.

(Cured Film Production Method)

The cured film production method according to the present embodiment includes a step (i) of forming a photosensitive resin film on a support using the above-described negative photosensitive resin composition according to the embodiment and a step (ii) of curing the photosensitive resin film to obtain a cured film.

The operation of the step (i) can be performed in the same manner as in Film formation step described above. The bake treatment can be performed, for example, under a temperature condition of 80° C. to 150° C. for 40 to 600 seconds.

The curing treatment in the step (ii) can be performed under the conditions of, for example, a temperature of 100° C. to 250° C. and 0.5 to 2 hours.

The cured film production method according to the embodiment may include other steps in addition to the step (i) and the step (ii). For example, Exposure step described above may be included between the step (i) and the step (ii), and it is possible to obtain a cured film by selectively exposing the photosensitive resin film formed in the step (i), and curing the photosensitive resin film (pre-cured film) to which a bake (PEB) treatment has been performed as necessary.

According to the above-described cured film production method according to the embodiment, a cured film which faithfully reproduces the mask pattern can be easily produced.

EXAMPLES

Hereinafter, the present invention will be described in more detail with reference to examples, but the present invention is not limited to these examples. "Part" in the description of each production example means part by mass.

<Production of Sulfonium Salt>

Production Example 1

Synthesis of [2-tert-butyl-5-methyl-4-(2-thioxanthonylthio)phenyl](5-tert-butyl-2-methylphenyl)(2-thioxanthonyl)sulfonium methane sulfonate (compound (I0-41))

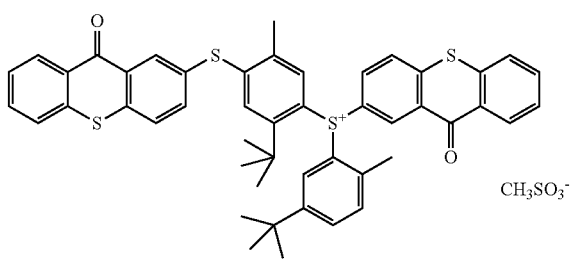

(I0-41)

CH$_3$SO$_3^-$ 1.0 part of 2-[(5-tert-butyl-2-methylphenyl)sulfinyl]thioxanthone, 1.0 part of 2-[(5-tert-butyl-2-methylphenyl)thio]thioxanthone, 5.0 parts of acetic anhydride, and 1.9 parts of methanesulfonic acid were homogeneously mixed and reacted at 65° C. for 6 hours. The reaction solution was cooled to room temperature, poured into 10 parts of ion exchange water, and extracted with 10 parts of dichloromethane. The aqueous phase was removed, and 10 parts of ion exchange water was again fed to wash the organic phase. The organic phase-washing operation was repeated until the pH of the aqueous phase is neutral. Thereafter, unreacted raw materials were eliminated by repeating three times a series of operations involving addition of 15 parts of cyclohexane to the organic phase, stirring, leaving at rest for 30 minutes, and removal of an upper phase. The lower phase was transferred to a rotary evaporator, and the solvent was evaporated to obtain 1.5 parts of a compound (I0-41).

The obtained compound (I0-41) was identified by $^1$H-NMR and LC-MS.

$^1$H-NMR: d6-dimethylsulfoxide, δ(ppm) 8.7 (1H, s), 8.2 to 8.5 (4H, m), 7.7 to 8.0 (8H, m), 7.5 to 7.6 (3H, m), 7.2 (2H, d), 7.0 (1H, s), 2.4 (3H, s), 2.3 (3H, s), 2.2 (3H, s), 1.3 (9H, s), 1.1 (9H, s) LC-MS: (positive) m/z=779.00, (negative) m/z=94.98

Production Example 2

Synthesis of [2-tert-butyl-5-methyl-4-(2-thioxanthonylthio)phenyl](5-tert-butyl-2-methylphenyl)(2-thioxanthonyl)sulfonium tris(pentafluoroethyl)trifluorophosphate (compound (I0-46))

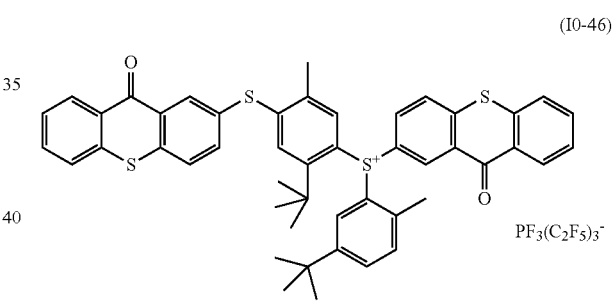

(I0-46)

PF$_3$(C$_2$F$_5$)$_3^-$ 1.0 parts of the compound (I0-41) synthesized in Production Example 1 was dissolved in 5.8 parts of dichloromethane, and 0.59 parts of potassium tris(pentafluoroethyl)trifluorophosphate and 5.1 parts of ion exchange water were added thereto, and the mixture was stirred at room temperature for 1 hour. The organic phase was washed five times with 5 parts of ion exchange water and transferred to a rotary evaporator, and the solvent was evaporated to obtain 1.26 parts of a compound (10-46).

The obtained compound (I0-46) was identified by $^1$H-NMR and $^{19}$F-NMR.

$^1$H-NMR: d6-dimethylsulfoxide, δ(ppm) 8.7 (1H, s), 8.2 to 8.5 (4H, m), 7.7 to 8.0 (8H, m), 7.5 to 7.6 (3H, m), 7.2 (2H, d), 7.0 (1H, s), 2.4 (3H, s), 2.2 (3H, s), 1.3 (9H, s), 1.1 (9H, s)

$^{19}$F-NMR: d6-dimethylsulfoxide, δ(ppm) −42.0 (1F, d), −79.9 (3F, s), −81.2 (6F, s), −87.9 (2F, d), −115.0 to −116.2 (6F, m)

Production Example 3

Synthesis of [2-tert-butyl-5-methyl-4-(2-thioxanthonylthio)phenyl](5-tert-butyl-2-methylphenyl)(2-thioxanthonyl)sulfonium tetrakis(pentafluorophenyl) borate (compound (I0-45))

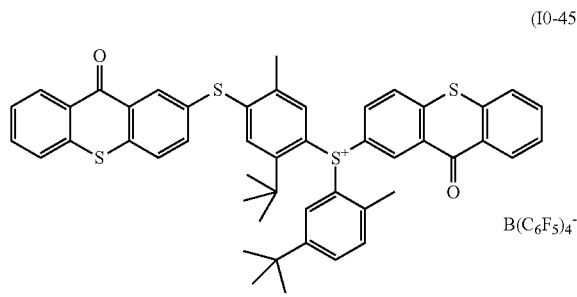

(I0-45)

1.5 parts of a compound (I0-45) was obtained in the same manner as in Production Example 2, except that, in Production Example 2, the "0.59 parts of potassium tris(pentafluoroethyl)trifluorophosphate" was changed to "0.85 parts of sodium tetrakis(pentafluorophenyl) borate".

The obtained compound (I0-45) was identified by $^1$H-NMR and $^{19}$F-NMR.

$^1$H-NMR: d6-dimethylsulfoxide, δ(ppm) 8.7 (1H, s), 8.2 to 8.5 (4H, m), 7.7 to 8.0 (8H, m), 7.5 to 7.6 (3H, m), 7.2 (2H, d), 7.0 (1H, s), 2.4 (3H, s), 2.2 (3H, s), 1.3 (9H, s), 1.1 (9H, s)

$^{19}$F-NMR: d6-dimethylsulfoxide, δ(ppm) −132.1 (8F, s), −161.8 (4F, s), −166.0 (8F, s)

Production Example 4

Synthesis of Compound (H1-TF)

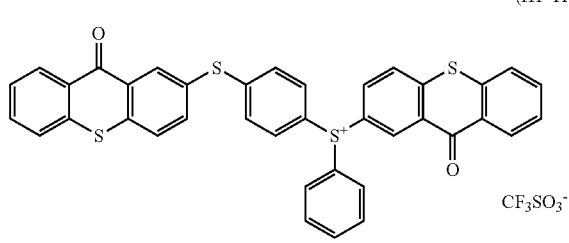

(H1-TF)

While 4.3 parts of 2-(phenylthio)thioxanthone, 4.5 parts of 2-[(phenyl)sulfinyl]thioxanthone, 4.1 parts of acetic anhydride, and 110 parts of acetonitrile were stirred at 40° C., 2.4 parts of trifluoromethanesulfonic acid was gradually dropwise added thereto. The mixture was reacted at 40° C. to 45° C. for 1 hour. The reaction solution was cooled to room temperature (approximately 25° C.), poured into 150 parts of distilled water, extracted with chloroform, and washed with water until the pH of the aqueous phase is neutral. The chloroform phase was transferred to a rotary evaporator, and the solvent was evaporated. The solid formed was washed by repeating three times a series of operations involving addition of 50 parts of toluene, dispersion in the toluene using an ultrasonic washer, leaving at rest for approximately 15 minutes, and removal of a supernatant. Next, the solid was transferred to a rotary evaporator, and the solvent was evaporated to obtain a compound (H$_1$-TF).

Production Example 5

Synthesis of compound (H1-FP)

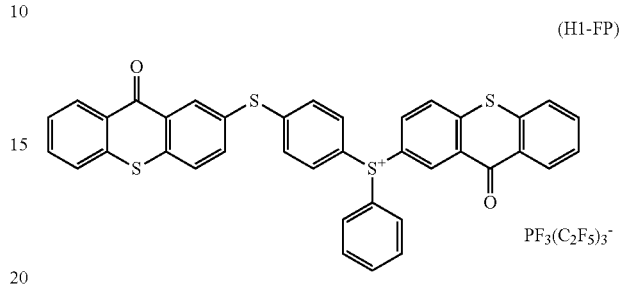

(H1-FP)

1.0 part of the compound (H$_1$-TF) was dissolved in 6.4 parts of dichloromethane. 0.60 parts of potassium tris(pentafluoroethyl)trifluorophosphate and 5.7 parts of ion exchange water were added thereto, and the mixture was stirred at room temperature for 1 hour. The organic phase was washed five times with 6 parts of ion exchange water and transferred to a rotary evaporator, and the solvent was evaporated to obtain 1.2 parts of a compound (H$_1$—FP). The obtained compound (H$_1$—FP) was identified by $^1$H-NMR and $^{19}$F-NMR.

$^1$H-NMR: d6-dimethylsulfoxide, δ(ppm) 8.7 (1H, d), 8.5 (1H, d), 8.4 (2H, m), 8.2 (1H, d), 8.1 (1H, dd), 8.0 (1H, d), 7.7 to 7.9 (12H, m), 7.6 (2H, m), 7.5 (2H, d)

$^{19}$F-NMR: d6-dimethylsulfoxide, δ(ppm) −42.0 (1F, d), −79.9 (3F, s), −81.2 (6F, s), −87.9 (2F, d), −115.0 to −116.2 (6F, m)

Production Example 6

Synthesis of Compound (H1-B)

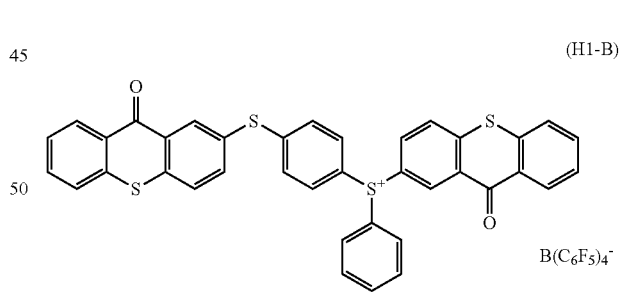

(H1-B)

1.5 parts of a compound (H$_1$—B) was obtained in the same manner as in Production Example 5, except that, in Production Example 5, the "0.60 parts of potassium tris(pentafluoroethyl)trifluorophosphate" was changed to "0.93 parts of sodium tetrakis(pentafluorophenyl) borate".

The obtained compound (H$_1$—B) was identified by $^1$H-NMR and $^{19}$F-NMR.

$^1$H-NMR: d6-dimethylsulfoxide, δ(ppm) 8.7 (1H, d), 8.5 (1H, d), 8.4 (2H, m), 8.2 (1H, d), 8.1 (1H, dd), 8.0 (1H, d), 7.7 to 7.9 (12H, m), 7.6 (2H, m), 7.5 (2H, d)

$^{19}$F-NMR: d6-dimethylsulfoxide, δ(ppm) −132.1 (8F, s), −161.8 (4F, s), −166.0 (8F, s)

Preparation of Negative Photosensitive Resin Composition

Examples 1 and 2 and Comparative Examples 1 and 2

Respective components listed in Table 1 were mixed and dissolved in each other, and the solution was filtered using a PTFE filter (a pore diameter of 1 μm, manufactured by Pall Corporation) to prepare each negative photosensitive resin composition (a solution having a solid content of 65% by mass) of each example.

TABLE 1

| | Component (A) | | Component (I) | | | Component (S) |
|---|---|---|---|---|---|---|
| Example 1 | (A)-1 [15] | (A)-2 [85] | (I)-1 [0.68] | — | (I)-5 [0.015] | (S)-1 [54] |
| Example 2 | (A)-1 [15] | (A)-2 [85] | (I)-2 [0.81] | — | (I)-5 [0.015] | (S)-1 [54] |
| Comparative Example 1 | (A)-1 [15] | (A)-2 [85] | — | (I)-3 [0.73] | (I)-5 [0.015] | (S)-1 [54] |
| Comparative Example 2 | (A)-1 [15] | (A)-2 [85] | — | (I)-4 [0.60] | (I)-5 [0.015] | (S)-1 [54] |

In Table 1, each abbreviation has the following meaning. The numerical values in the parentheses are the blending amount (parts by mass, in terms of solid content) of the respective components.

(A)-1: novolak-type epoxy resin represented by General Formula (A11); trade name "JER157S70", manufactured by Mitsubishi Chemical Corporation

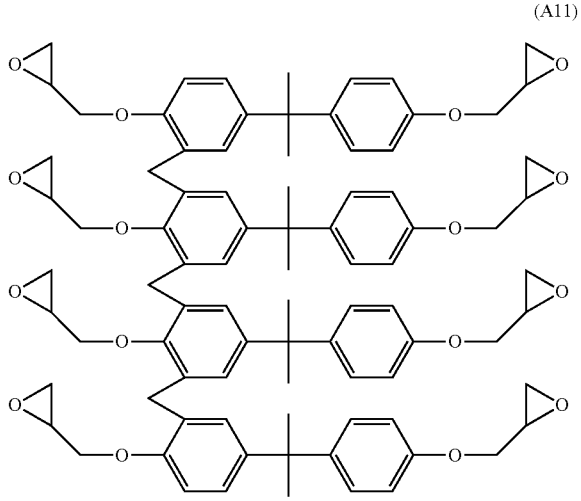

(A11)

(A)-2: bisphenol A-type epoxy resin represented by General Formula (A21); trade name "EPICLON 1055", manufactured by DIC Corporation; in Formula (A21), n is the number of repetitions of a structure in the parentheses

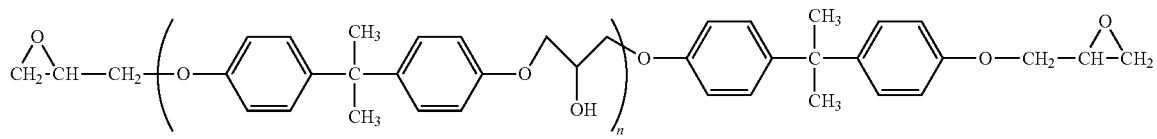

(A21)

(I)-1: compound (I0-46) described above
(I)-2: compound (I0-45) described above
(I)-3: compound (H₁—B) described above; that is, a cationic polymerization initiator represented by Chemical Formula (I1-1)
(I)-4: compound (H₁—FP) described above; that is, a cationic polymerization initiator represented by Chemical Formula (I2-1)

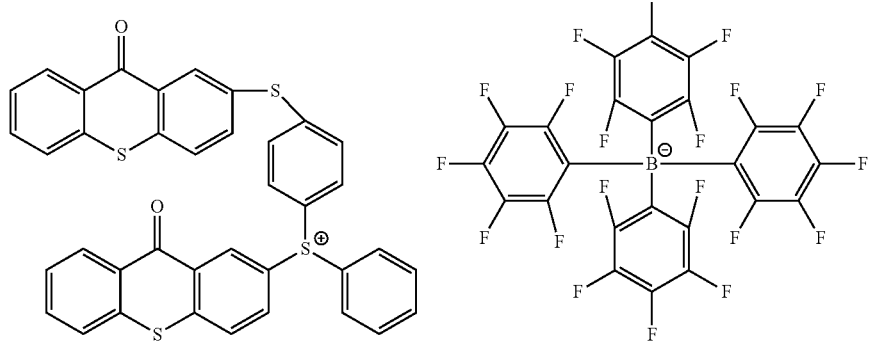

(I1-1)

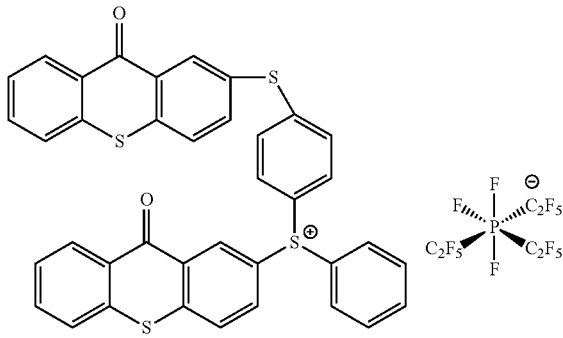

(I2-1)

(I)-5: cationic polymerization initiator represented by Chemical Formula (I3-1)

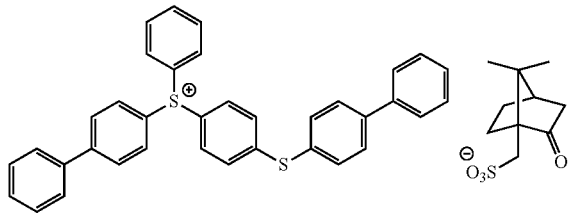

(I3-1)

(S)-1: methoxybutyl acetate

<Pattern Formation (1)>

Film Formation Step:

The negative photosensitive resin composition of each example was applied to a lithium tantalate (LiTaO$_3$) substrate having a thickness of 0.35 mm using a spinner, subjected to a pre-bake treatment (PAB) on a hot plate at a temperature of 115° C. for 5 minutes, and dried to form a photosensitive resin film having a film thickness of 20 μm.

Exposure Step:

Next, the above-described photosensitive resin film was irradiated with ghi-line at an irradiation amount of 350 mJ/cm$^2$. Thereafter, on a hot plate at 90° C., heating was performed after the exposure for 15 minutes.

Development Step:

Next, using propylene glycol monomethyl ether acetate (PGMEA), development was performed for 180 seconds to attempt a formation of a negative pattern.

<Pattern Formation (2)>

Film Formation Step:

The negative photosensitive resin composition of each example was applied to a lithium niobate (LiNbO$_3$) substrate having a thickness of 0.35 mm using a spinner, subjected to a pre-bake treatment (PAB) on a hot plate at a temperature of 115° C. for 5 minutes, and dried to form a photosensitive resin film having a film thickness of 20 μm.

Exposure Step:

Next, the above-described photosensitive resin film was exposed to light of 350 mJ/cm$^2$ in terms of i-line using a ghi broadband exposure device through a photomask.

Thereafter, on a hot plate at 90° C., heating was performed after the exposure for 15 minutes.

Development Step:

Next, using propylene glycol monomethyl ether acetate (PGMEA), development was performed for 30 seconds to attempt a formation of a negative pattern.

[Mask Reproducibility]

By the pattern formation (1) and pattern formation (2) described above, a contact hole (C/H) pattern was formed at an exposure amount of 350 mJ/cm$^2$ with a target size of 20 μm in hole diameter. The results were as follows.

In case of pattern formation (1): lithium tantalate (LiTaO$_3$) substrate

Example 1: C/H pattern with a hole diameter of 19.418 μm was formed.

Example 2: C/H pattern with a hole diameter of 17.887 μm was formed.

Comparative Example 1: no image was formed (poor resolution).

Comparative Example 2: no image was formed (poor resolution).

In case of pattern formation (2): lithium niobate (LiNbO$_3$) substrate

Example 1: C/H pattern with a hole diameter of 20.356 μm was formed.

Example 2: C/H pattern with a hole diameter of 19.944 μm was formed.

Comparative Example 1: C/H pattern with a hole diameter of 17.540 μm was formed.

Comparative Example 2: C/H pattern with a hole diameter of 16.582 μm was formed.

[Maximum Resolution]

In each exposure step of the pattern formation (1) and pattern formation (2) described above, the C/H pattern was formed by changing the exposure amount by 50 mJ/cm$^2$ in a range of 250 to 600 mJ/cm$^2$, and the minimum pattern dimension resolved at each exposure amount was determined using a scanning electron microscope S—9380 (manufactured by Hitachi High-Tech Corporation).

The results at an exposure amount of 350 mJ/cm$^2$ were as follows.

In case of pattern formation (1): lithium tantalate (LiTaO$_3$) substrate

Example 1: C/H pattern with a hole diameter of up to 10 μm was formed.

Example 2: C/H pattern with a hole diameter of up to 15 μm was formed.

Comparative Example 1: no image was formed (poor resolution).

Comparative Example 2: C/H pattern with a hole diameter of up to 40 μm was formed.

In addition, with regard to the negative photosensitive resin composition of Example 1, a C/H pattern with a hole diameter of up to 10 μm could be formed at an exposure amount in a range of 350 to 450 mJ/cm$^2$.

With regard to the negative photosensitive resin composition of Example 2, a C/H pattern with a hole diameter of up to 15 μm could be formed at an exposure amount in a range of 300 to 400 mJ/cm².

From the results, it could be confirmed that the negative photosensitive resin compositions of Examples 1 and 2 were excellent in exposure margin.

In case of pattern formation (2): lithium niobate (LiNbO₃) substrate

Example 2: C/H pattern with a hole diameter of up to 10 μm was formed.

Comparative Example 1: C/H pattern with a hole diameter of up to 20 μm was formed.

In addition, with regard to the negative photosensitive resin composition of Example 2, a C/H pattern with a hole diameter of up to 5 μm could be formed at an exposure amount in a range of 250 to 300 mJ/cm².

From the result, it could be confirmed that the negative photosensitive resin composition of Example 2 was particularly excellent in resolution.

From the above evaluation results, compared to the negative photosensitive resin compositions of Comparative Examples 1 and 2, which were outside of the scope of the present invention, it could be confirmed that the negative photosensitive resin compositions of Examples 1 and 2, to which the present invention was adopted, had a higher resolution.

What is claimed is:

1. A negative photosensitive resin composition comprising:
   an epoxy group-containing resin (A); and
   a cationic polymerization initiator (I),
   wherein the cationic polymerization initiator (I) includes a sulfonium salt (I0) represented by General Formula (I0),

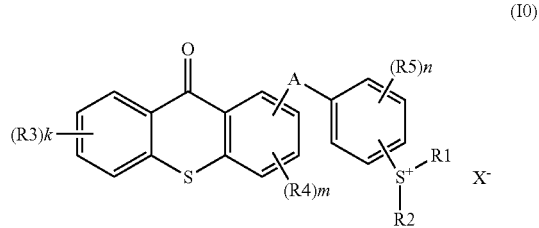

(I0)

wherein in Formula (I0), R1 represents a thioxanthonyl group; R2 represents an aryl group having 6 to 30 carbon atoms, in which a part of hydrogen atoms in the aryl group is substituted with a substituent (t), the substituent (t) being at least one selected from the group consisting of an alkyl group having 1 to 18 carbon atoms or an alkoxy group having 1 to 18 carbon atoms, R3 to R5 are each an alkyl group or an alkoxy group, k, m, and n represent the numbers of R3, R4, and R5, in which k is an integer of 0 to 4, m is an integer of 0 to 3, and n is an integer of 1 to 4, in a case where each of k, m, and n is 2 or more, a plurality of R3's, R4's, or R5's may be the same or different from each other, A is a group represented by —S—, —O—, —SO—, —SO₂—, or —CO—, O is an oxygen atom, S is a sulfur atom, and X⁻ represents a monovalent polyatomic anion.

2. The negative photosensitive resin composition according to claim 1, wherein A in General Formula (I0) is a group represented by —S— or —O—, and each of k and m is 0 and n is an integer of 1 to 4.

3. The negative photosensitive resin composition according to claim 1,
   wherein in General Formula (I0)
   each of k and m is 0 and n is 1 or 2, and
   A is a group represented by —S—.

4. The negative photosensitive resin composition according to claim 1, wherein X⁻ in General Formula (I0) is an anion represented by $(Rf)_b PF_{6-b}^-$ or $R^6{}_c BY_{4-c}^-$, wherein Rf represents an alkyl group in which 80 mol % or more of hydrogen atoms are substituted with fluorine atoms, $R^6$ represents a phenyl group in which a part of hydrogen atoms are substituted with at least one halogen atom or electron-withdrawing group, Y represents a halogen atom, b is an integer of 1 to 5, and c is an integer of 1 to 4.

5. The negative photosensitive resin composition according to claim 1, wherein a content of the sulfonium salt (I0) is 0.1 to 5 parts by mass with respect to 100 parts by mass of the epoxy group-containing resin (A).

6. The negative photosensitive resin composition according to claim 1, wherein the epoxy group-containing resin (A) includes a resin having a glycidyl ether group in a structure of the resin.

7. The negative photosensitive resin composition according to claim 1, wherein the epoxy group-containing resin (A) includes both a novolak-type epoxy resin and a bisphenol A-type epoxy resin.

8. A pattern formation method comprising:
   forming a photosensitive resin film on a support using the negative photosensitive resin composition according to claim 1;
   exposing the photosensitive resin film; and
   developing the exposed photosensitive resin film with a developing solution containing an organic solvent to form a negative pattern.

9. A laminated film comprising:
   a support film, and
   a photosensitive resin composition layer laminated on the support film,
   wherein the photosensitive resin composition layer is formed from the negative photosensitive resin composition according to claim 1.

10. The negative photosensitive resin composition according to claim 1, wherein X⁻ in General Formula (I0) is an anion represented by $R^6{}_c BY_{4-c}^-$, wherein $R^6$ represents a phenyl group in which a part of hydrogen atoms are substituted with at least one halogen atom or electron-withdrawing group, Y represents a halogen atom, and c is an integer of 1 to 4.

* * * * *